US012678329B2

(12) United States Patent
    Horvath

(10) Patent No.:  US 12,678,329 B2
(45) Date of Patent:       Jul. 14, 2026

(54) SYSTEMS AND METHODS FOR TREATING GLAUCOMA WITH LASER PULSES AND VISUALIZING THE ANTERIOR ANGLE OF THE EYE

(71) Applicant: EYEX SOLUTIONS INC., San Juan Capistrano, CA (US)

(72) Inventor: Christopher Horvath, San Juan Capistrano, CA (US)

(73) Assignee: EyeX Solutions Inc., San Juan Capistrano, CA (US)

( * ) Notice: Subject to any disclaimer, the term of this patent is extended or adjusted under 35 U.S.C. 154(b) by 119 days.

(21) Appl. No.: 18/234,382

(22) Filed: Aug. 16, 2023

(65) Prior Publication Data

US 2024/0058170 A1    Feb. 22, 2024

Related U.S. Application Data

(60) Provisional application No. 63/399,996, filed on Aug. 22, 2022.

(51) Int. Cl.
    *A61F 9/008*            (2006.01)
(52) U.S. Cl.
    CPC .... *A61F 9/008* (2013.01); *A61F 2009/00851* (2013.01); *A61F 2009/00861* (2013.01); *A61F 2009/00891* (2013.01)
(58) Field of Classification Search
    CPC .. A61F 2009/00844; A61F 2009/00851; A61F 2009/00861; A61F 2009/00868; A61F 2009/00891; A61F 9/008; A61F 9/00825
    See application file for complete search history.

(56) References Cited

U.S. PATENT DOCUMENTS

| | | | |
|---|---|---|---|
| 6,547,394 B2 | 4/2003 | Doherty | |
| 8,446,341 B2 | 5/2013 | Amirparviz et al. | |
| 8,740,383 B2 | 6/2014 | Yates | |
| 8,798,332 B2 | 8/2014 | Otis et al. | |

(Continued)

FOREIGN PATENT DOCUMENTS

| | | |
|---|---|---|
| EP | 2459050 | 6/2012 |
| EP | 3009093 | 4/2016 |

(Continued)

OTHER PUBLICATIONS

Robert, FM et al., "VCSEL pair used as optical pointers in a contact lens for gaze tracking and visual target designation" (2022) PLOS One 17(7): e0267393. https://doi.org/10.1371/journal.pone.0267393.

*Primary Examiner* — Scott Luan
(74) *Attorney, Agent, or Firm* — Morgan, Lewis & Bockius LLP

(57)                ABSTRACT

A laser system for treating target tissue layers of an anterior chamber angle of an eye, including a delivery system and various imaging systems is being disclosed here. The system includes novel configurations using small digital cameras, OCT and other diagnostic devices that are integrated with a goniolens to visualize and target the to be treated tissue layers and that in some configurations remain connected and active during the laser treatment. Furthermore, several novel illumination systems and standalone digital camera goniolens systems are being presented here.

20 Claims, 26 Drawing Sheets

(56) References Cited

U.S. PATENT DOCUMENTS

| | | | |
|---|---|---|---|
| 8,945,103 B2 | 2/2015 | Chew et al. | |
| 9,265,410 B2 | 2/2016 | Yates | |
| 9,265,656 B2 | 2/2016 | Yee | |
| 9,278,029 B2 | 3/2016 | Yee et al. | |
| 9,289,123 B2 | 3/2016 | Weibel et al. | |
| 9,320,460 B2 | 4/2016 | Liu et al. | |
| 9,459,469 B2 | 10/2016 | Markus | |
| 9,962,071 B2 | 5/2018 | Yates | |
| 10,258,233 B2 | 4/2019 | Benner et al. | |
| 10,359,648 B2 | 7/2019 | Kim et al. | |
| 10,426,330 B2 | 10/2019 | Yates | |
| 10,663,760 B2 | 5/2020 | Heacock | |
| 10,674,906 B2 | 6/2020 | Kalina, Jr. et al. | |
| 10,744,033 B2 | 8/2020 | Baerveldt et al. | |
| 11,033,184 B2 | 6/2021 | Yates | |
| 11,246,754 B2 | 2/2022 | Holland et al. | |
| 11,744,458 B2 | 9/2023 | Kalina, Jr. et al. | |
| 11,819,271 B2 | 11/2023 | Yates | |
| 12,067,933 B2 | 8/2024 | Hekmat et al. | |
| 12,544,590 B2 | 2/2026 | Chen | |
| 2011/0213342 A1* | 9/2011 | Tripathi | A61B 34/20 600/425 |
| 2017/0290508 A1 | 10/2017 | Vadakke Matham et al. | |
| 2018/0078129 A1* | 3/2018 | Vadakke Matham | G02B 21/0076 |
| 2018/0235462 A1* | 8/2018 | Gooi | A61B 3/16 |
| 2023/0320900 A1 | 10/2023 | Bor et al. | |

FOREIGN PATENT DOCUMENTS

| | | | |
|---|---|---|---|
| FR | 2970573 | 7/2012 | |
| WO | WO-2009158517 A2 * | 12/2009 | A61B 3/117 |
| WO | 2017137982 A1 | 8/2017 | |
| WO | WO-2018049359 A1 * | 3/2018 | A61B 3/117 |
| WO | WO-2019103631 A1 * | 5/2019 | A61B 3/117 |

* cited by examiner

SYSTEMS AND METHODS FOR TREATING GLAUCOMA WITH LASER PULSES AND VISUALIZING THE ANTERIOR ANGLE OF THE EYE

BACKGROUND AND BRIEF SUMMARY OF THE INVENTIONS

Lasers have been used for several decades in the treatment of glaucoma. The 2 most common laser treatments for primary open angle glaucoma (POAG) are ALT (Argon Laser Trabeculoplasty) and SLT (Selective Laser Trabeculoplasty). See, for example, U.S. Pat. Nos. 3,884,236; 8,066, 696; 5,549,596; and 6,319,274. They work by applying laser pulses into the trabecular meshwork located in the anterior angle 7913 of the eye also sometimes referred to as anterior chamber angle or irido-corneal angle. These laser pulses are focused to around 50 micrometer diameter for ALT and around 400 micrometer for SLT. Those laser spots are targeted to lay over the trabecular meshwork and increase outflow through the treated meshwork area into the Schlemm's canal by modulating the tissue properties. In both procedures at least 90 degrees of the anterior angle of the eye is treated with typically 180 degrees and 50 to 100 laser pulses (each pulse is applied to a new target zone-treatment area). The working mechanism for ALT is blanching of the trabecular meshwork that increases the outflow by stretching the trabecular meshwork between the blanched (laser treated areas). The ALT laser with a typical setting of 600 mW and 0.1 s pulse duration (at 514 nm or 532 nm) causes a thermal tissue interaction. In SLT treatment the laser causes cavitation bubbles in the target tissue due to its shorter pulse duration of about 3 nanoseconds and higher peak power (created by pulse energies of around 0.3 mJ to 1.6 mJ).

Both procedures have a good success rate by increasing aqueous humor outflow that creates a substantial drop in intraocular pressure of around 20%. Both procedures can be performed in minutes with a simple slit lamp procedure in the office (no operating room required). In both procedures, the eye does not need to be opened (non-invasive procedure, no incisions needed), therefore the treatment risks and complication rates are minimal. The problem of these procedures as published in many studies is that it does not work effectively in all patients and in the successful cases the effect wears off over the course of a few years (1-3 years) and the IOP rises overtime. The procedure can be repeated once with ALT and 2-3 times with SLT, but after those repeats the tissue damage in the trabecular meshwork that is created through those multiple procedures ultimately prevents any further IOP lowering effect.

A less frequently used laser procedure called ELT (Excimer Laser Trabeculostomy) uses an excimer laser pulse (wavelength in the UV range) to actually drill holes into the trabecular meshwork. See, for example, U.S. Patent Application Nos.: 20080082078; 20040082939. Because complete openings are created to Schlemm's canal (unlike ALT and SLT), the IOP lowering effect is similar or better than ALT/SLT and at the same time only a few open holes need to be drilled with ELT versus 50-100 treatment zones in a typical ALT/SL T procedure. Some studies further suggest that the ELT effect is longer lasting then ALT/SL T due to some observed long-term patency of those holes. Furthermore, ELT might be repeated more often since a smaller area of the trabecular meshwork is treated each time. The downside of ELT is the fact that UV wavelength light does not penetrate the cornea and aqueous humor, therefore the laser can only be applied to the trabecular meshwork in a sterile operating room, where the eye is opened and a fiber probe is inserted into the anterior chamber all the way up to the trabecular meshwork.

In recent years the effectiveness of having one or multiple holes in the trabecular meshwork (connecting to Schlemm's canal) has also been demonstrated with several implants, placed through the trabecular meshwork that creates a connection of the anterior chamber to Schlemm's canal, bypassing the meshwork. Another surgical method to remove, cut or incise part or all of the trabecular meshwork is called Goniotomy or Trabeculotomy often done by inserting a mechanical device into the eye. See, for example, U.S. Patent Application Nos.: 20120071809, 20070276316. Those are, however, also invasive (sterile operating room required) procedures using an implant or a surgical tool inside the eye.

Another approach to drain aqueous humor out of the anterior chamber has been successfully demonstrated by implanting a drainage tube through the scleral spur region and into the suprachoroidal space. See, for example, U.S. patent application No. 20110098629. This is, however, also an invasive (sterile operating room required) procedures using an implant.

Most recently, there have been animal tissue studies and initial human trials done by Vialase applying ultrashort photodisruptive laser pulses to the trabecular meshwork with good success. See, for example: Vialase in Opthtalmology Times, Sep. 21, 2021.

However, large challenges and areas of improvement remain within the area of delivering ultrashort laser pulses to the trabecular meshwork, due to the existing complexity and high cost of such laser systems and also due to the difficulty in visualizing and targeting the anterior angle tissues of the eye.

The inventions described herein relate to new devices and methods to overcome those limitations and challenges and therefore allow the creation of holes, open sections and channels (Goniotomy, Trabeculotomy or Trabeculostomy) in the trabecular meshwork and other places in the anterior angle area of an eye also referred to as irido-corneal angle of an eye or within this patent specifications referred to as the target area or target region or target tissue layers. This procedure when performed as a standalone procedure, is done in a non-invasive approach meaning no opening of the eye is performed. The procedure can therefore also be performed in a non-sterile office environment. These here described systems and methods reduce complexity, improve visualization and targeting of the angle tissue and can be repeated many times over as needed.

FIG. 28 shows the anterior angle area of a normal eye. The trabecular meshwork 7907 can be separated in a lower pigmented section 7910 and the upper non-pigmented section 7905. The lower pigmented part is thicker than the upper part and measures about 150 μm to 300 μm in thickness. The trabecular meshwork consists of 3 separately defined layers. Starting deeper inside the eye and moving outwards, there is the uveal meshwork 7930, the corneo-scleral meshwork 7935 and the juxtacanalicular tissue layer 7940. A healthy Meshwork lets the aqueous humor flow through from the anterior chamber 7912 into Schlemm's canal 7945. As the liquid propagates through these three tissue layers it encounters growing flow resistance until it finally flows through the inner wall of Schlemm's canal 7945 and then through Schlemm's canal until it exits through a collector channel 7925. Schlemm's canal goes around the entire 360 degrees of the eye angle, but is not a complete open tube but contains many septums and elastic bands, that create a pumping contraction to push the aqueous humor along. There are also narrowing segments along is circumference. Flow of aqueous humor will therefore not be equal in both directions once the aqueous humor reaches Schlemm's canal. Furthermore, the on average about 25-30 collector channels around the eye circumference are not equally placed in all eye quadrants but have a higher density in the nasal region of the eye. Therefore, the here described trabecular meshwork opening creation via laser is preferably performed in the nasal region of the eye.

The trabecular meshwork cannot be considered a simple shaped open tube. Especially in advanced stages of glaucoma Schlemm's canal starts to collapse as shown in FIG. 27, 7945. This makes targeting Schlemm's canal more difficult. Including a 3D imaging system in the laser treatment system helps identifying the shape, size and location of Schlemm's canal and the other eye features. In all cases, Schlemm's canal is mostly located behind the pigmented part 7910 of the trabecular meshwork which represents the lower part of the angle tissue area and therefore the laser system described here focuses on visualizing, identifying and targeting that region for best access to Schlemm's canal.

The target region area volume is defined as all or part of the volume within the following dimensions, see FIG. 28:

Z-axis: from the anterior chamber 7912 through the most inner, first trabecular meshwork layer (uveal) 7930 through all other layers towards and into Schlemm's canal 7945.

Y: from or below the scleral spur 7915 or relative to that upwards to Schwabe's line 7900 or above the pigmented part of trabecular meshwork 7905 or relative to either.

X: along the circumference of the anterior chamber angle 7913 as wide of an arc opening in the eye as desired, including multiple holes or full 360.

The inventions described herein relate to new devices and methods to:

Use one or multiple integrated digital cameras in the delivery system path for fs laser. Therefore, eliminating the need for a slit lamp or surgical microscope or any other integrated visual microscope. Furthermore, the camera is mounted next to a gonio lens and in some embodiments integrates with or within the goniolens as a detachable subunit of the delivery system or as a complete separate device.

When a camera is integrated with a gonio lens, then that subsystem can optionally be detached and used for diagnostic purposes separately.

A standalone Gonio lens with attached and or integrated camera and various advanced lighting systems.

A camera integrated Gonio-lens for pre-op, immediately before laser fires (final confirmation), during laser firing and post op visualization of the angle tissue.

Mirrored goniolens embodiments and direct goniolens embodiments integrated with digital Cameras.

Multiple illumination systems. Infrared, visible wavelengths, low light, specific wavelength settings and direct light to the retina for iris contraction or dilation.

Multiple delivery system integrated 3D visualization systems.

A system using an OCT (Optical Coherence Tomography) imaging beam over the target area and through the limbus area to locate and visualize Schlemm's canal. This system is integrated with the laser treatment system and is also a standalone diagnostic system that is used without surgery. This system is used pre-op, immediate before firing, during laser firing and post-op.

Automatic detection and selection of targeting area as well as user interface selected laser target via crosshair on computer screen showing the camera visualization of the target area.

Various illumination techniques by selecting and changing the illumination source wavelengths to highlight and enhance contrast of various target tissue layers and features.

Related prior art are U.S. Pat. Nos. 9,033,963; 14,685, 955; 8,056,564; 4,391,275; 5,288,288; 11,382,794, 7,912, 100; and 11,246,754, and all references cited therein and more.

SUMMARY OF THE FIGURES

The accompanying drawings, which are included to provide further understanding of the subject technology, are incorporated in and constitute a part of this specification. The drawings illustrate embodiments of the subject technology and, together with the description, serve to explain the principles of the subject technology. The drawings contain the following figures.

5

Figure 13:
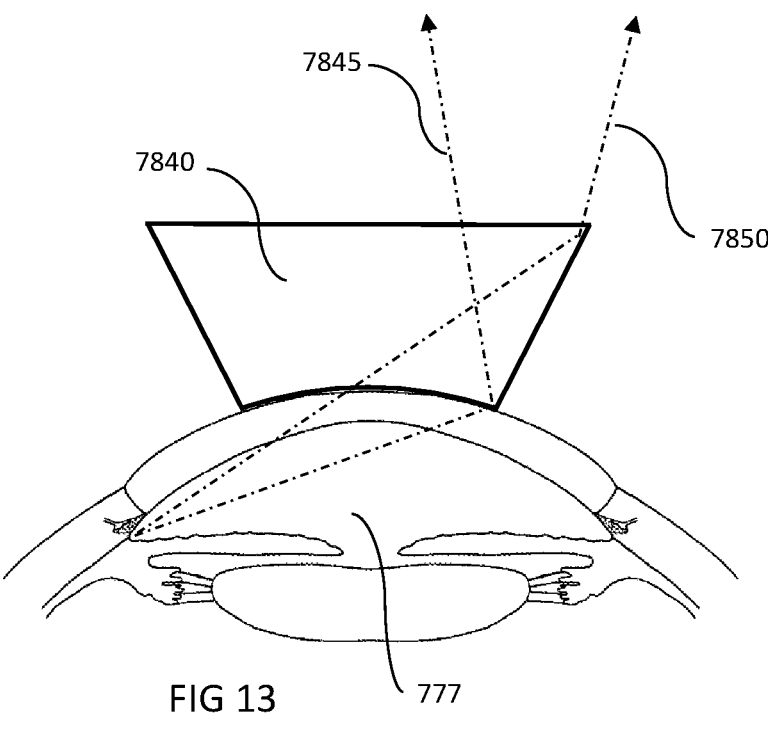

FIG. 13 is a cross-sectional view of an anterior portion of an eye showing illumination beams directed at a target area from above the eye through a goniolens, according to some embodiments.

Figure 14:
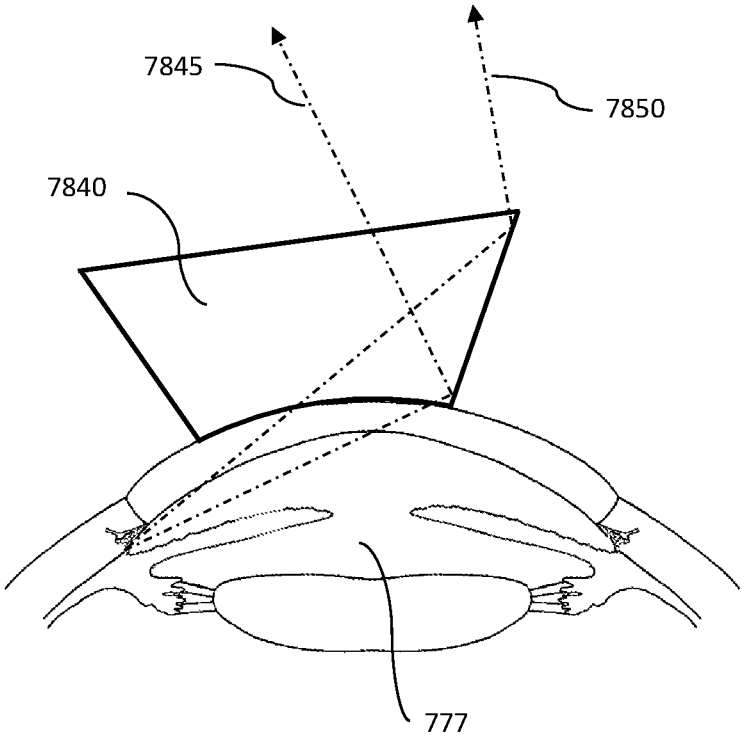

FIG. 14 is a cross-sectional view of an anterior portion of an eye showing illumination beams directed at a target area from above the eye through a goniolens, according to another embodiment.

Figure 15:
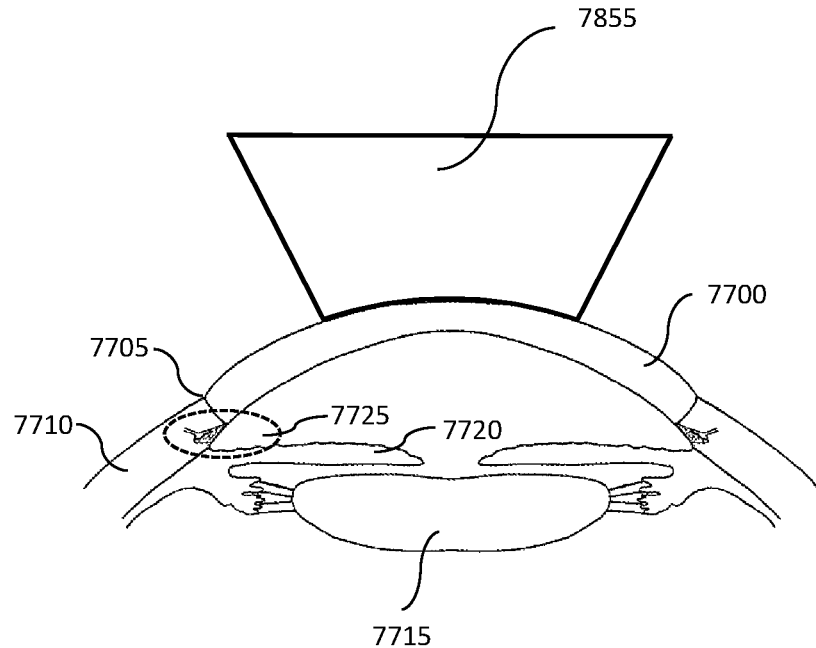

FIG. 15 is a cross-sectional view of an anterior portion of an eye with a goniolens placed on the cornea, according to some embodiments.

Figure 16:
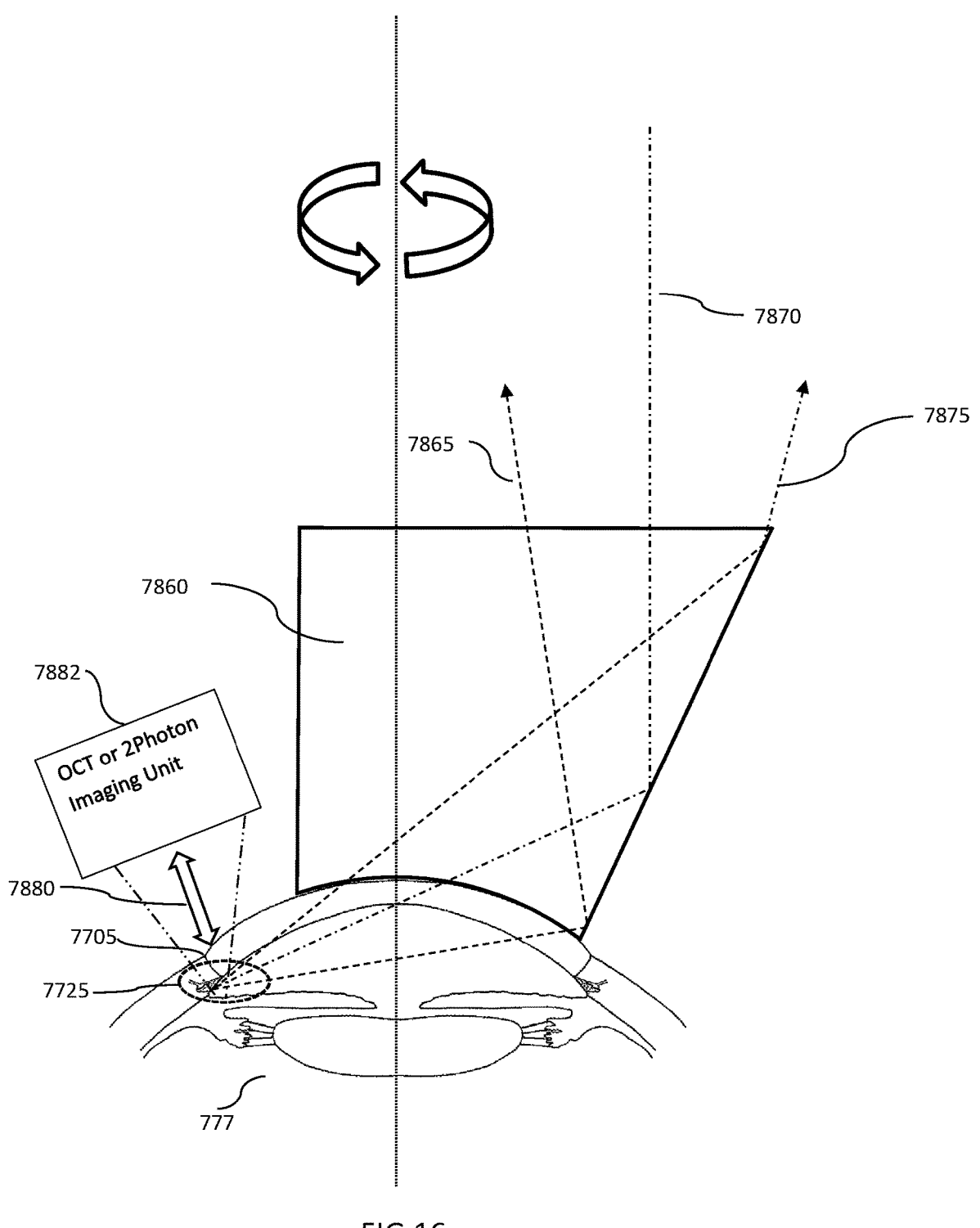

FIG. 16 is a schematic view of a laser treatment system with an OCT or two-photon imaging unit entering the eye through an entry area on the limbus, according to some embodiments.

Figure 17:
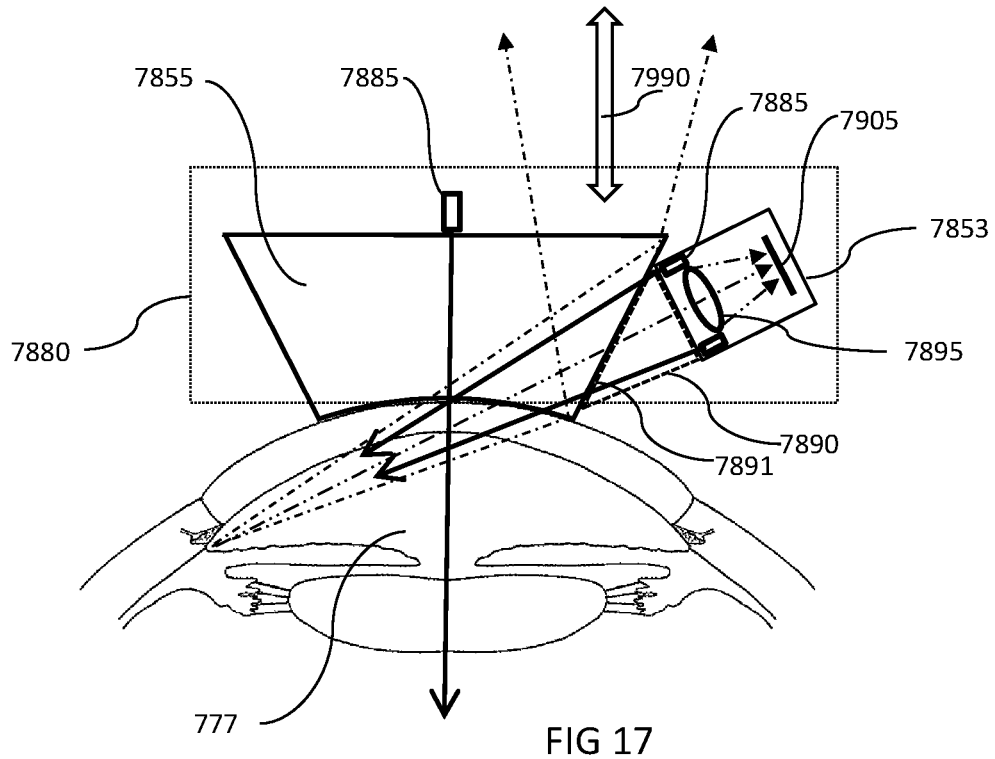

FIG. 17 is a schematic view of a laser treatment system with a one-piece mirrored goniolens including an optional digital camera or illumination source coupled to the goniolens, and showing treatment and diagnostic beams extending into the goniolens and eye via a mirror, according to some embodiments.

Figure 18:
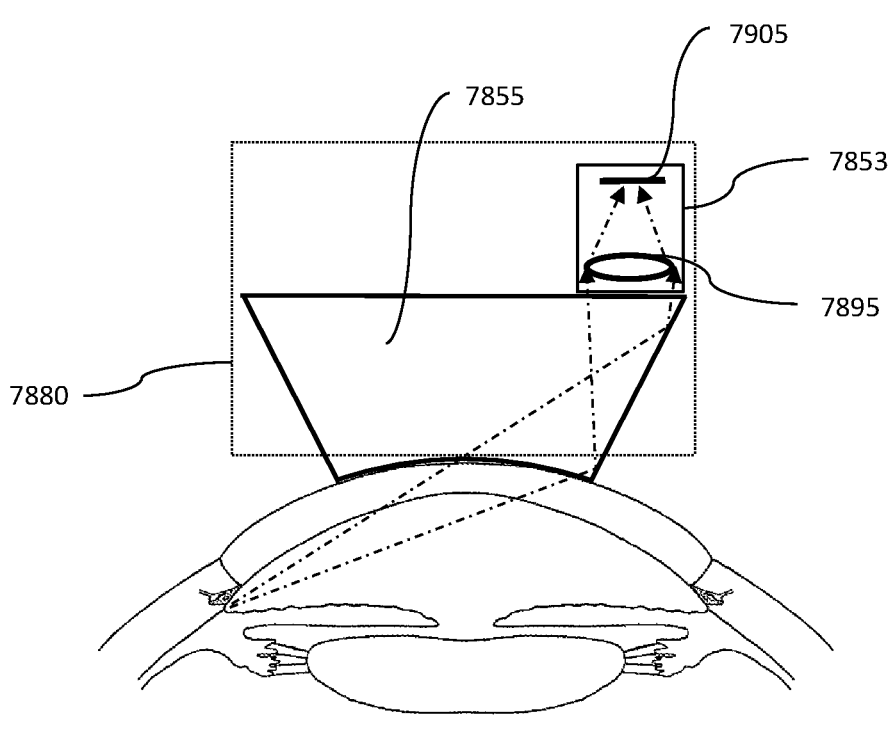

FIG. 18 is a schematic view of a laser treatment system with a camera unit coupled to a goniolens, according to some embodiments.

Figure 18B:
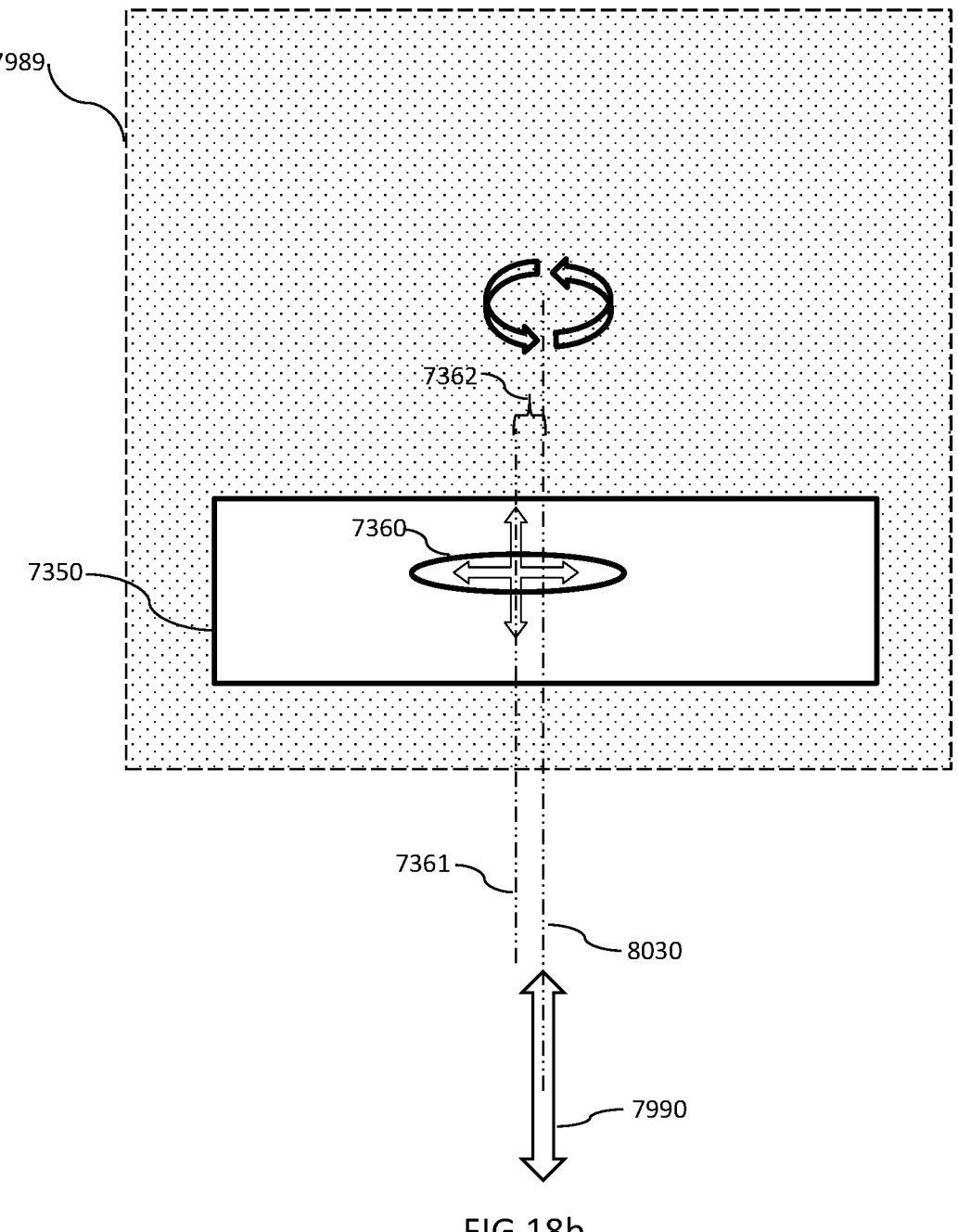

FIG. 18*b* is a schematic view of a focusing and optional scanning unit of the delivery system, according to some embodiments.

Figure 19:
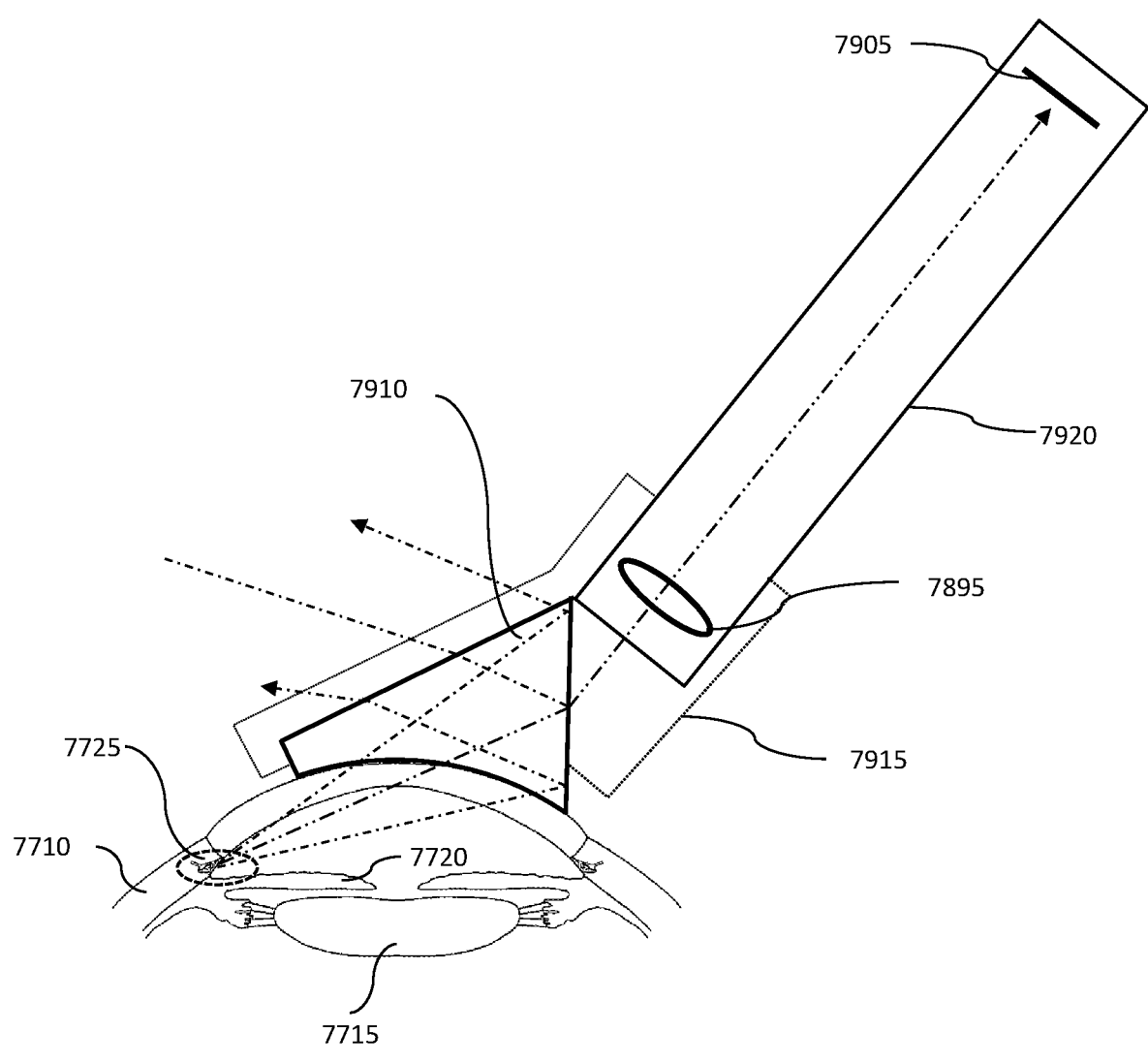

FIG. 19 is a schematic view of a camera unit coupled to a goniolens, according to some embodiments.

Figure 20:
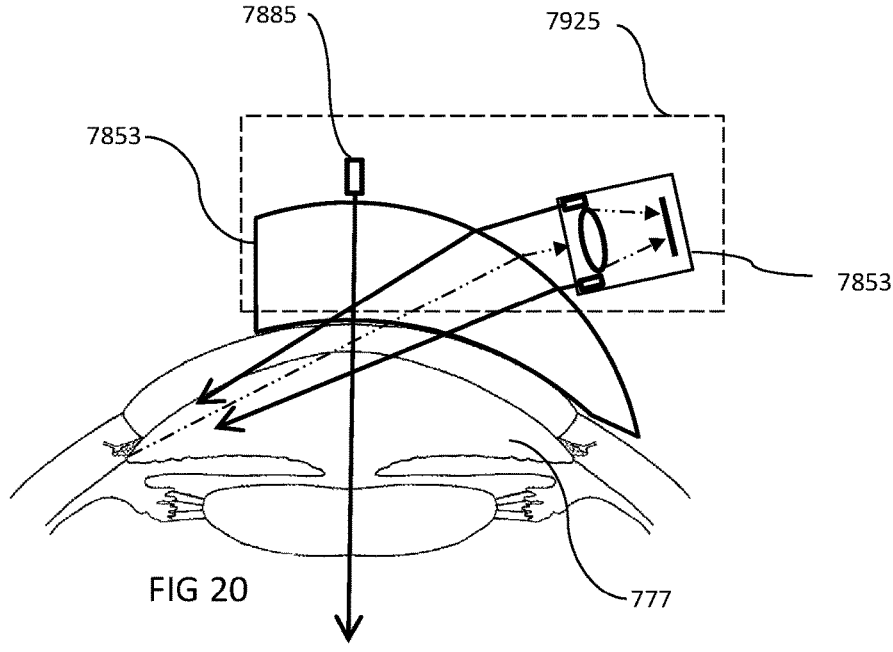

FIG. 20 is a schematic view of an optional camera and illumination unit connected to a goniolens and placed on the eye, according to some embodiments.

Figure 21:
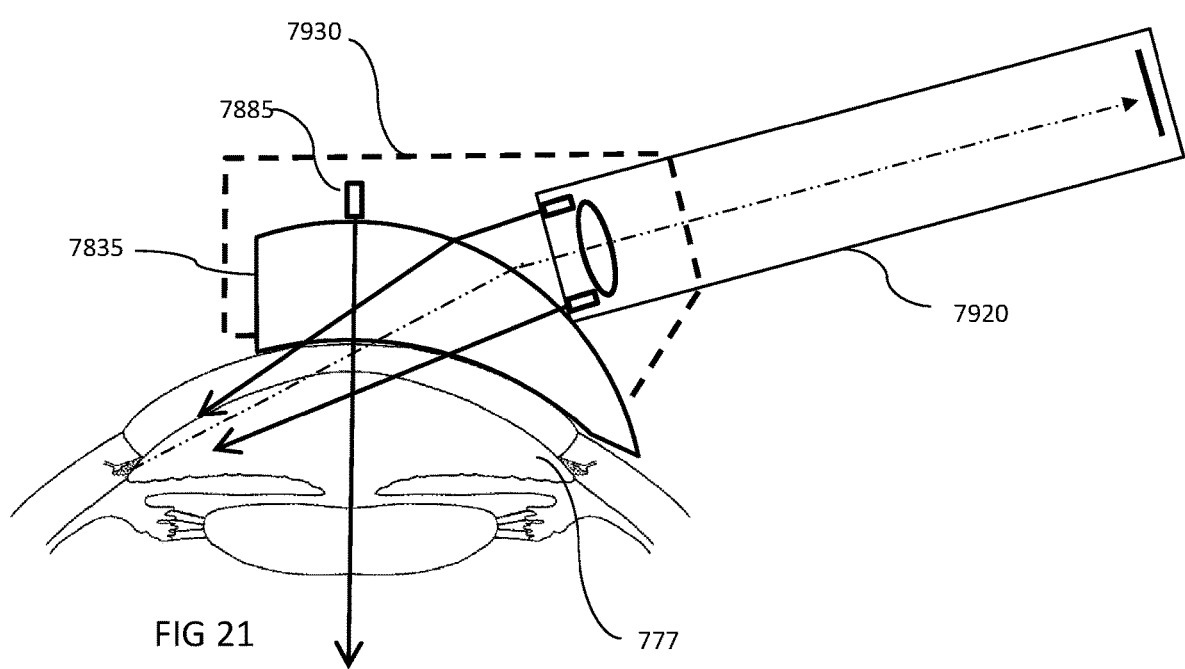

FIG. 21 is a schematic view of an optional camera and illumination unit coupled to a goniolens, according to some embodiments.

Figure 22:
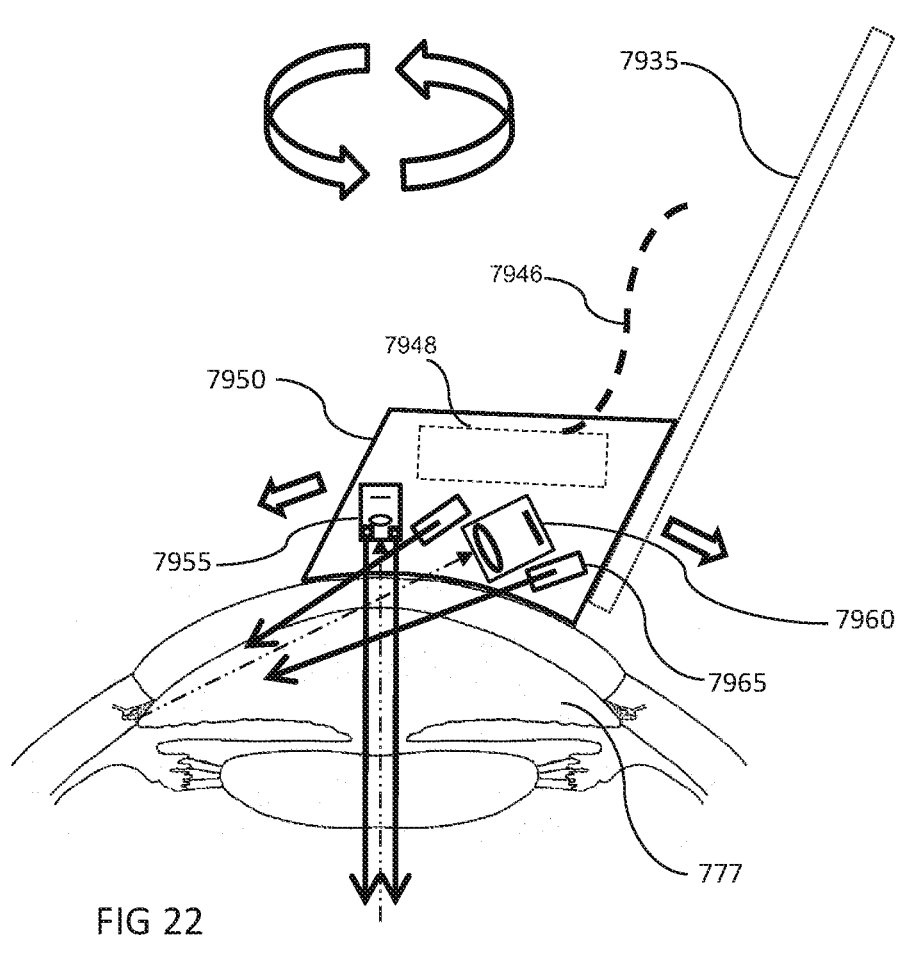

FIG. 22 is a schematic view of a gonio unit having a camera and/or an illumination source and an optional handle, according to some embodiments.

Figure 23:
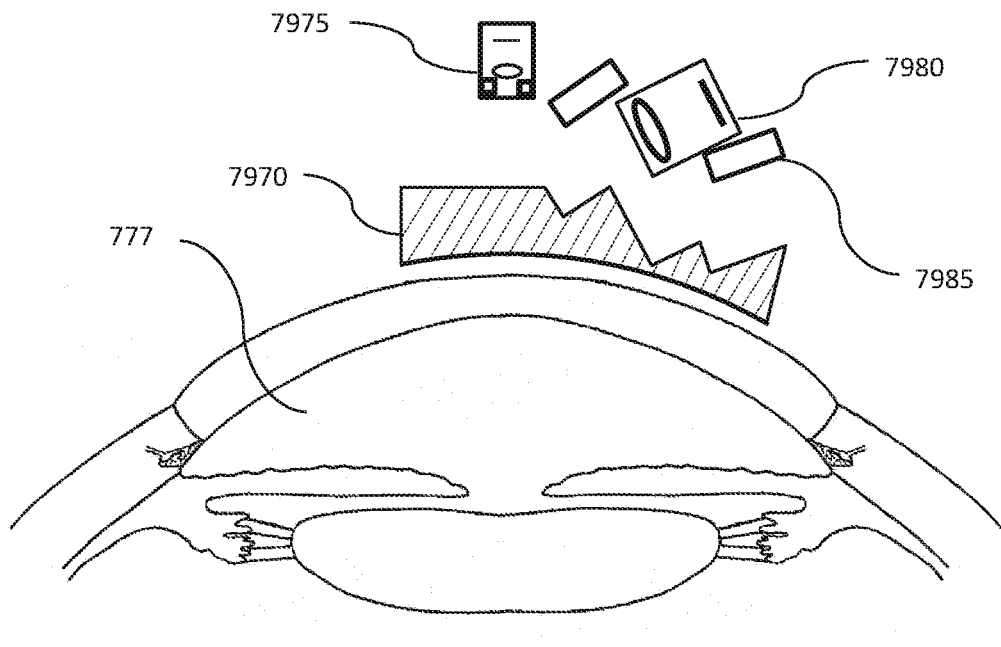

FIG. 23 is a schematic view of a gonio unit having a camera and/or an illumination source, according to some embodiments.

Figure 24:
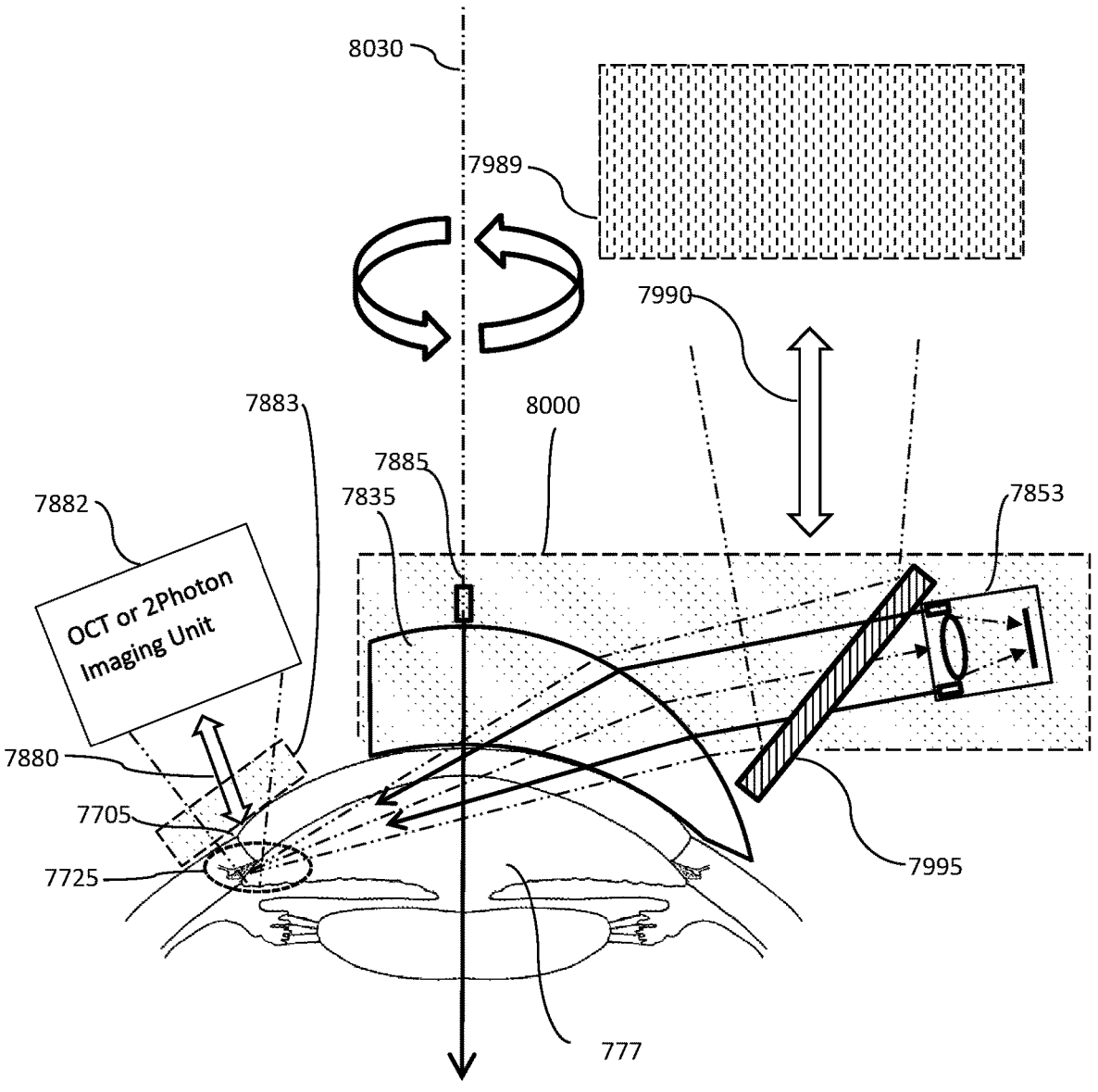

FIG. 24 is a schematic view of a laser treatment system where a treatment laser beam enters the eye through a goniolens from one side while an OCT or two-photon imaging beam and a camera with illumination enter the eye from another side through a cutout in the goniolens, according to some embodiments.

Figure 25:
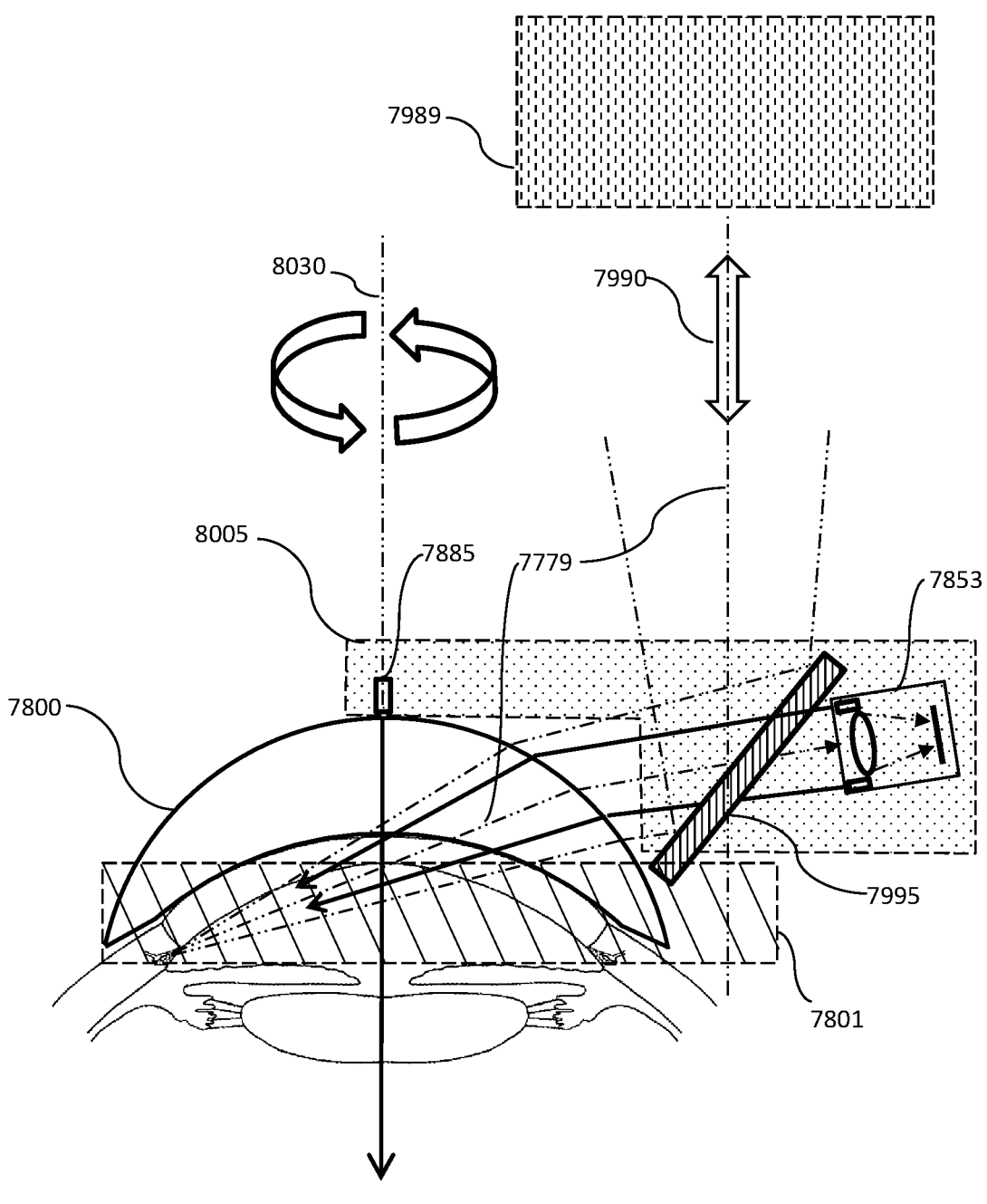

FIG. 25 is a schematic view of a laser treatment system similar to FIG. 24, showing a delivery system with a laser delivery system, a treatment beam, and an imaging beam path entering a goniolens with an optional camera and illumination unit, according to some embodiments.

Figure 26:
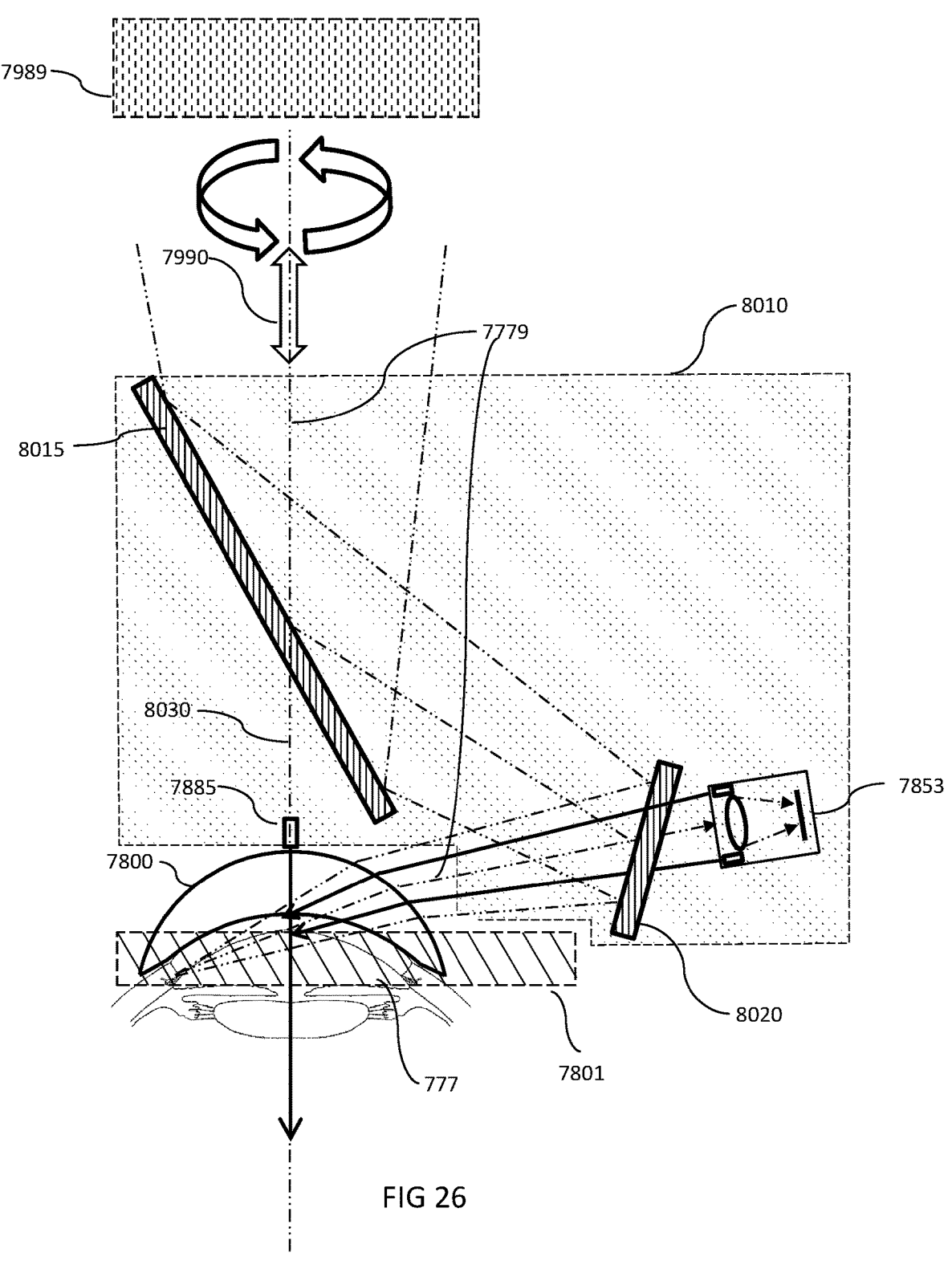

FIG. 26 is a schematic view of a laser treatment system with a laser delivery system, two routing mirrors, and a goniolens with an optional camera and illumination unit, according to some embodiments.

Figure 27:
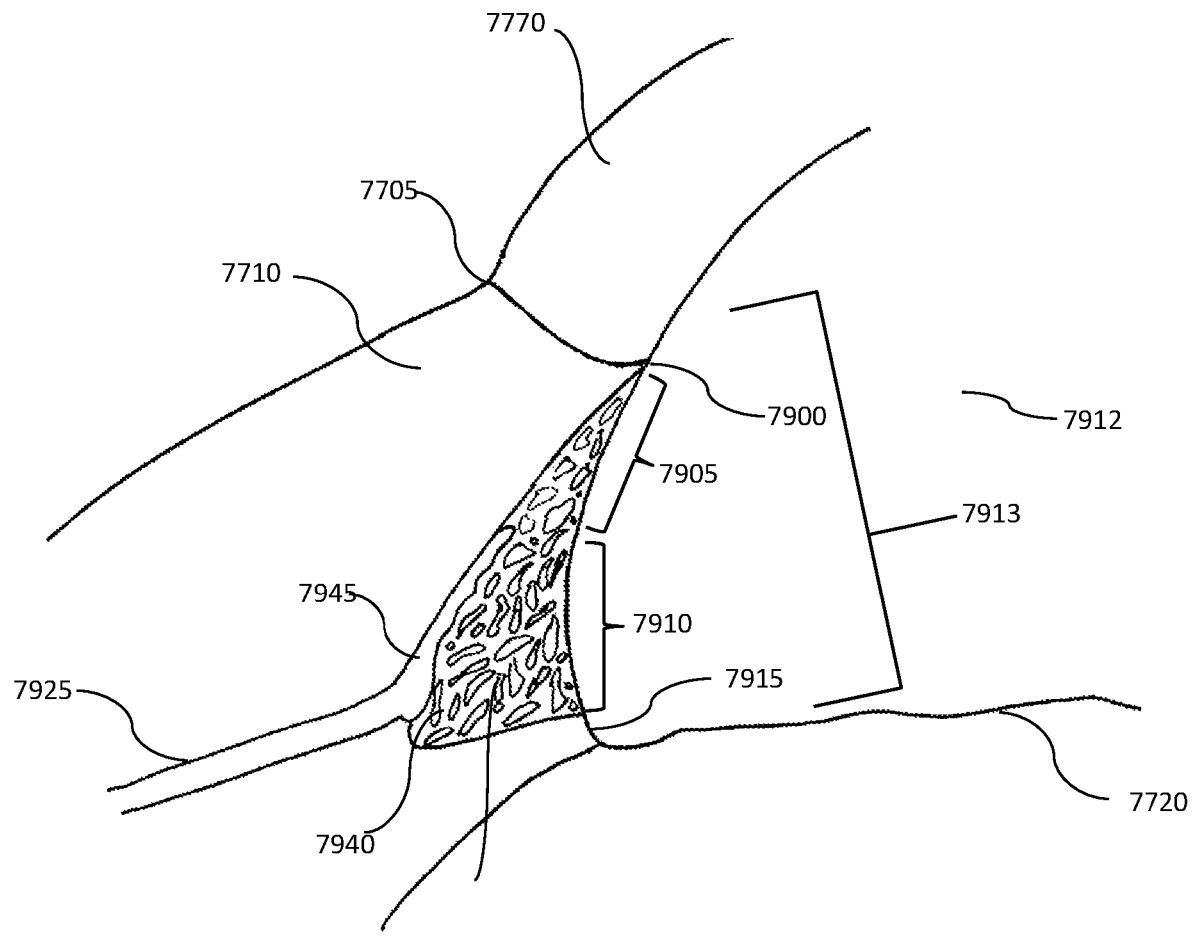

FIG. 27 is a cross-sectional view of an anterior angle area of a normal eye, showing the cornea, iris, trabecular meshwork layers including the uveal meshwork, the corneoscleral meshwork, and the juxtacanalicular tissue layer, Schlemm's canal, a collector channel, and the scleral spur, according to some embodiments.

Figure 28:
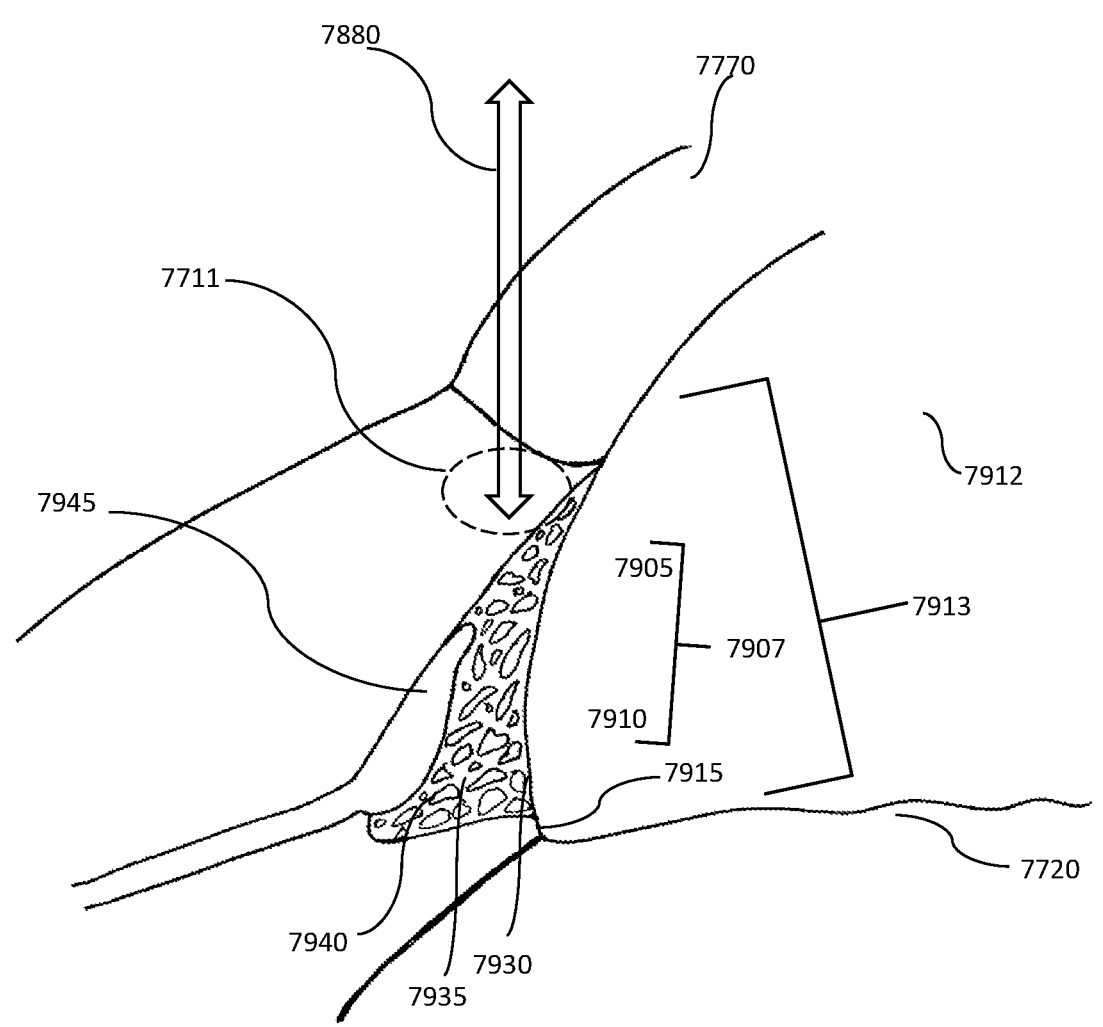

FIG. 28 is a cross-sectional view of an anterior angle area of the eye showing an OCT or diagnostic imaging beam entering the eye through a transition zone between the cornea and sclera to image the trabecular meshwork layers and Schlemm's canal. according to some embodiments.

6

Figure 29:
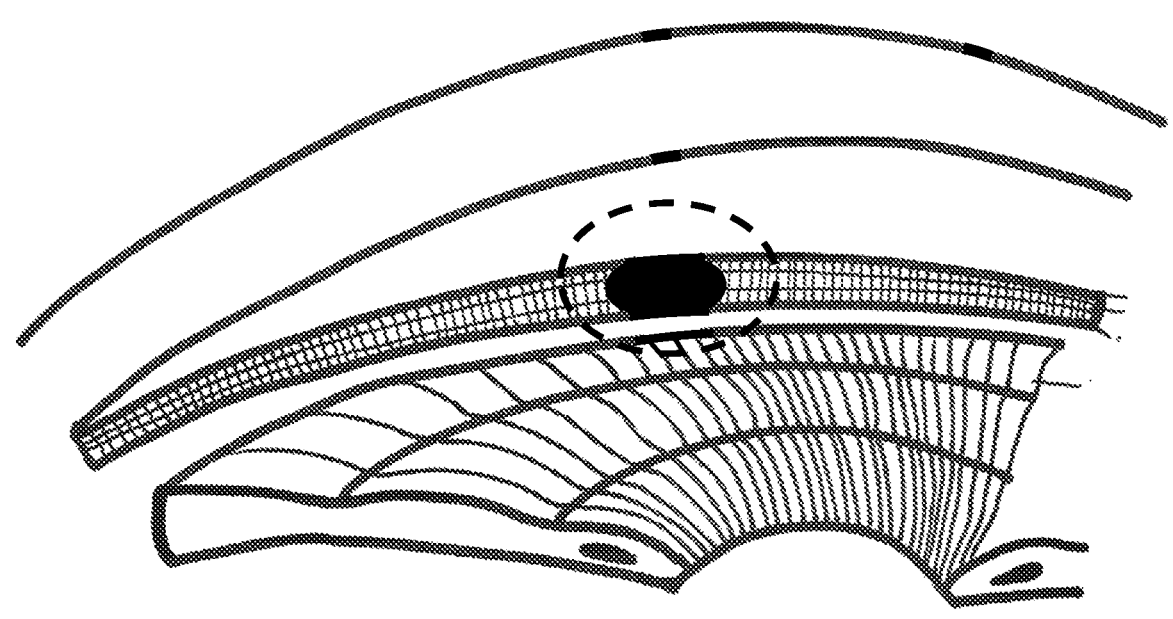

FIG. 29 is a close-up cross-sectional view of the anterior angle tissue of the eye showing a laser treatment spot on the trabecular meshwork, according to some embodiments.

DETAILED DESCRIPTION OF THE INVENTIONS AND CLAIMS

A laser system to create opening channels and open sections through the trabecular meshwork of an eye to allow aqueous humor to flow through those openings into Schlemm's canal and from there continue through at least part of Schlemm's canal and at least partially further out of the anterior eye chamber via collector channels and thereby reducing the pressure in the Eye and therefore treating Glaucoma.

Figure 1:
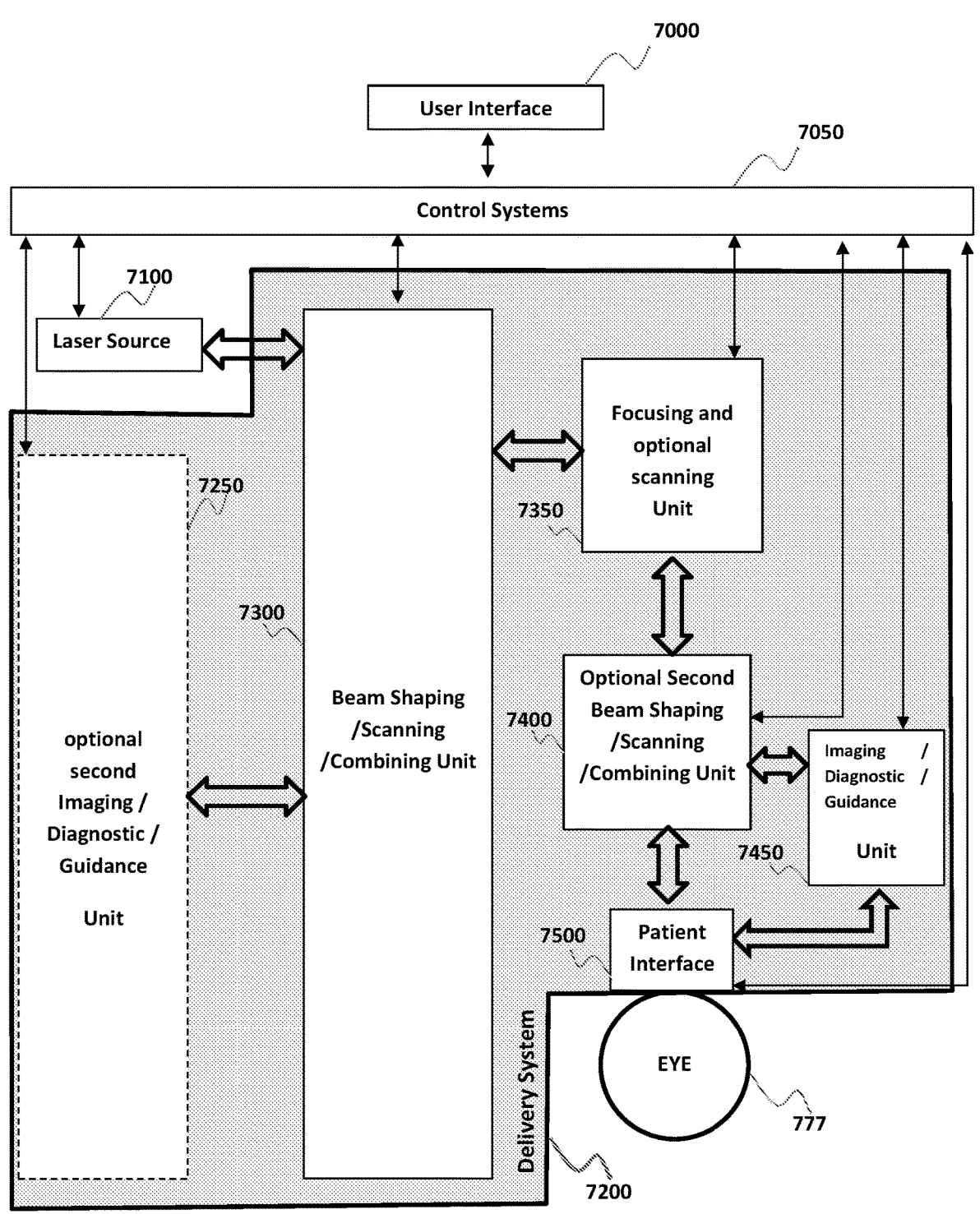
FIG. 1 is a block diagram of a laser system for treating target tissue layers of an anterior chamber angle of an eye in a minimal configuration, according to some embodiments.
Figure 2:
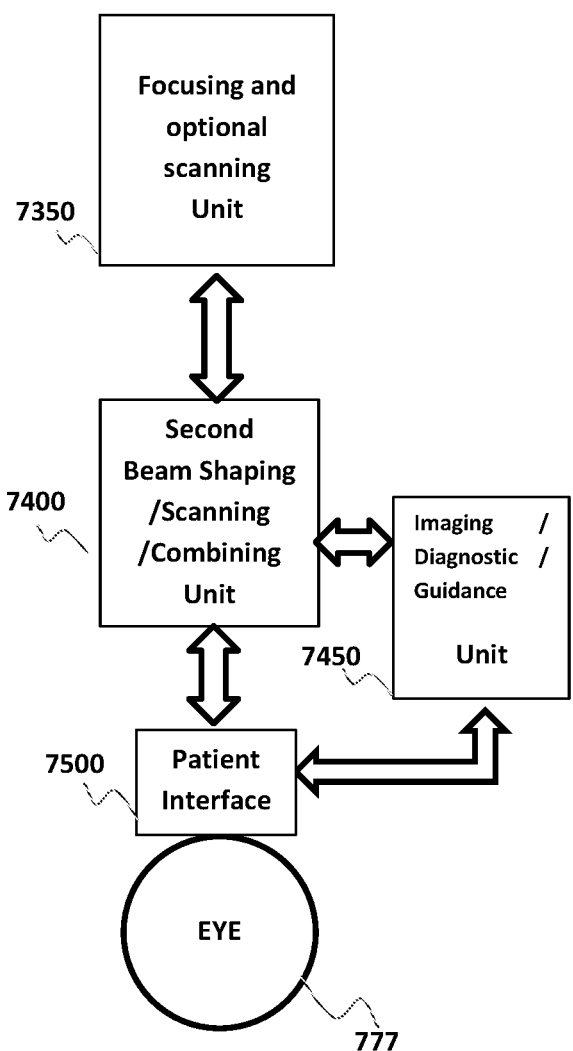
FIG. 2 is a block diagram of a portion of a delivery system of the laser system of FIG. 1, showing a focusing and optional scanning unit, a second beam shaping, scanning and combining unit, an imaging, diagnostic and guidance unit, a patient interface, and an eye, according to some embodiments.

A laser system in its most minimal configuration consisting of FIG. 1:

User interface 7000
Control system 7050
Laser source 7100
Delivery system 7200

Where each one of the sub-units named above is a placeholder for describing one or multiple units. E.g., The Unit: Laser Source 7100 includes either one laser source or multiple laser sources. Same is true with User Interface 7000 which can consist either of a single user interface or multiple separate user interfaces and so on.

Where the User Interface 7000 consists of at least one of the following:

An input foot or hand switch (operated by a human foot or hand) with a single switch or a multi control input foot or hand switch with several switches and adjustment input abilities such as multidimensional joystick capabilities or other input systems.

A foot or hand switch as above further including several feedback (output) mechanisms, each one of them informing the operator of various states and parameters of the laser system before, during and after the treatment procedure. This feedback mechanism consists of at least one of the following:

One or multiple visual feedbacks such as lights with various colors, brightness and blinking patterns. For example, red, green and yellow indication lights static on, off or blinking.

One or multiple displays integrated into the foot or hand switch.

One or multiple tactile feedback systems using mechanical vibrations of various strength, frequency and timing. For example, if the laser system is in a warning or error state the foot or hand switch could start vibrating to inform the operator.

One or multiple audio feedback systems, such as beeping or other tone generators or voice feedback with a specific message for the operator. For example, the system may say: "System ready" or "Treatment complete" based on the status of the system.

One or several computer screens or touch screens for input and output of visualization, other data and commands.

A computer.

A keyboard, mouse or any other computer user interface.

Where the control system 7050 consists of at least one of the following:

A computer, electronics boards to power, control and process input and output data of the laser sources, the user interface and all subsystems of the delivery system.

Where the laser source 7100 consists of at least one of the following:

A laser engine producing ultrashort laser pulse with a pulse duration between 100 femtosecond and 50 nanoseconds, a pulse energy between 1 μJ (MicroJoule) and 5000 μJ (5 mJ), a pulse repetition rate between single shot and 500 kHz and a wavelength between 350 nm and 1600 nm.

Figure 3:
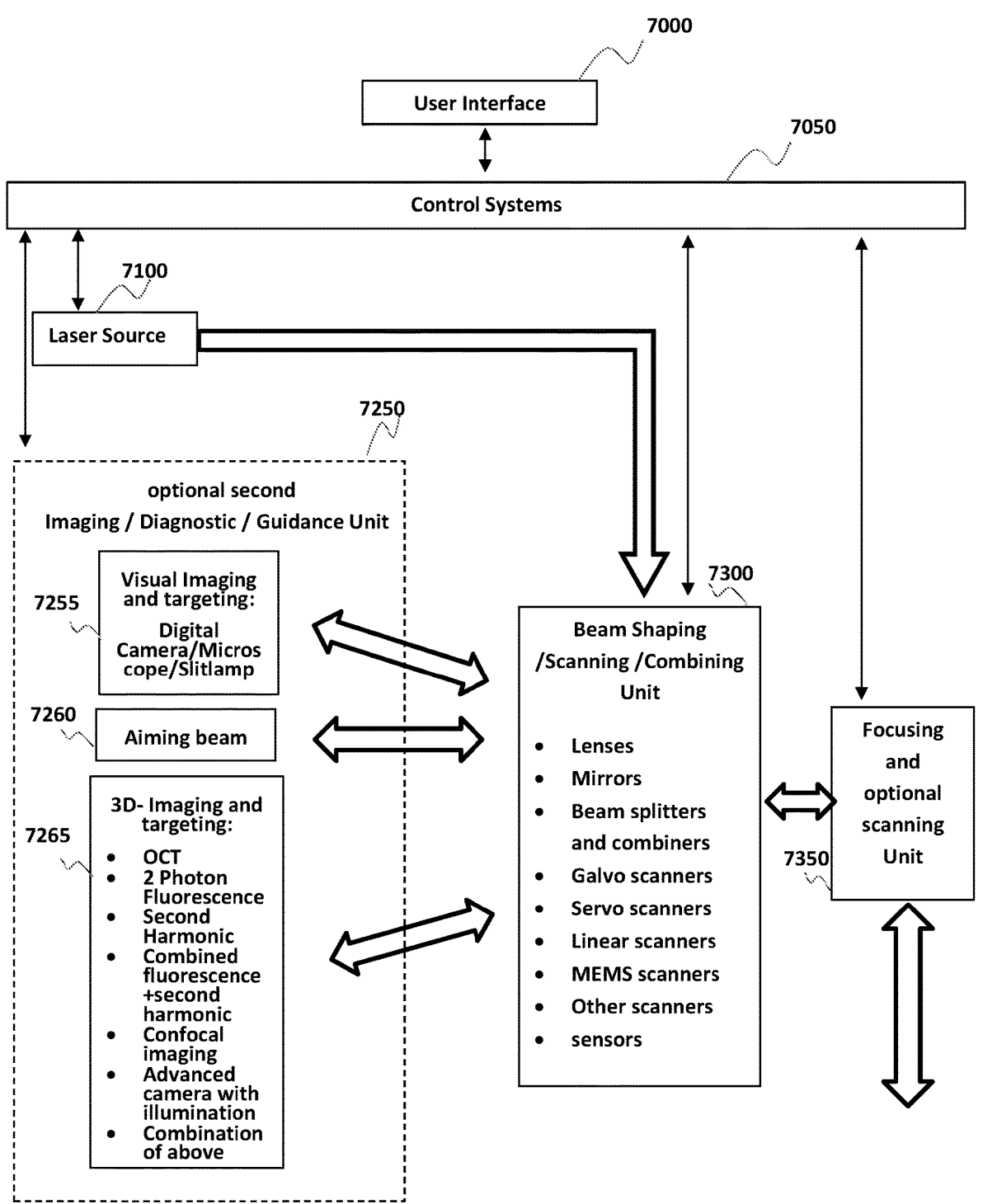
FIG. 3 is a block diagram of a laser system showing details of an optional second imaging, diagnostic and guidance unit and a beam shaping, scanning and combining unit, according to some embodiments.
Figure 4:
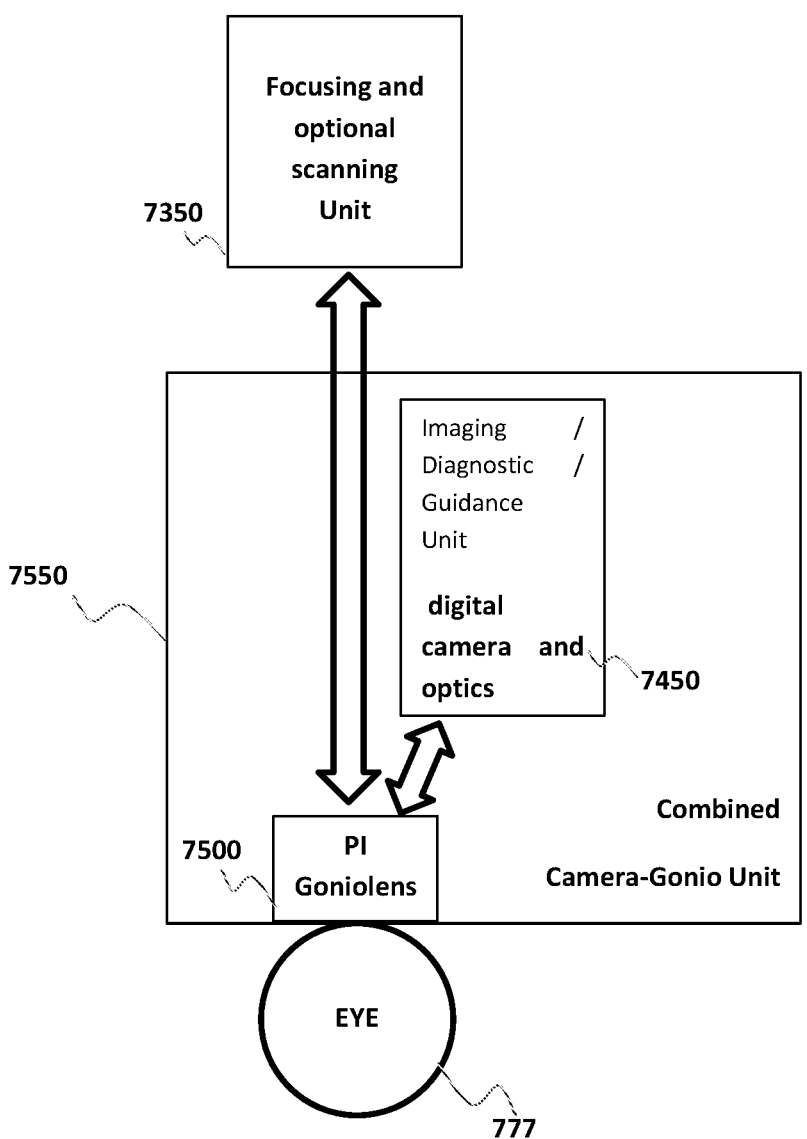
FIG. 4 is a block diagram of a combined camera-gonio unit including a focusing and optional scanning unit, an imaging, diagnostic and guidance unit with a digital camera and optics, and a patient interface goniolens, according to some embodiments.
Figure 5:
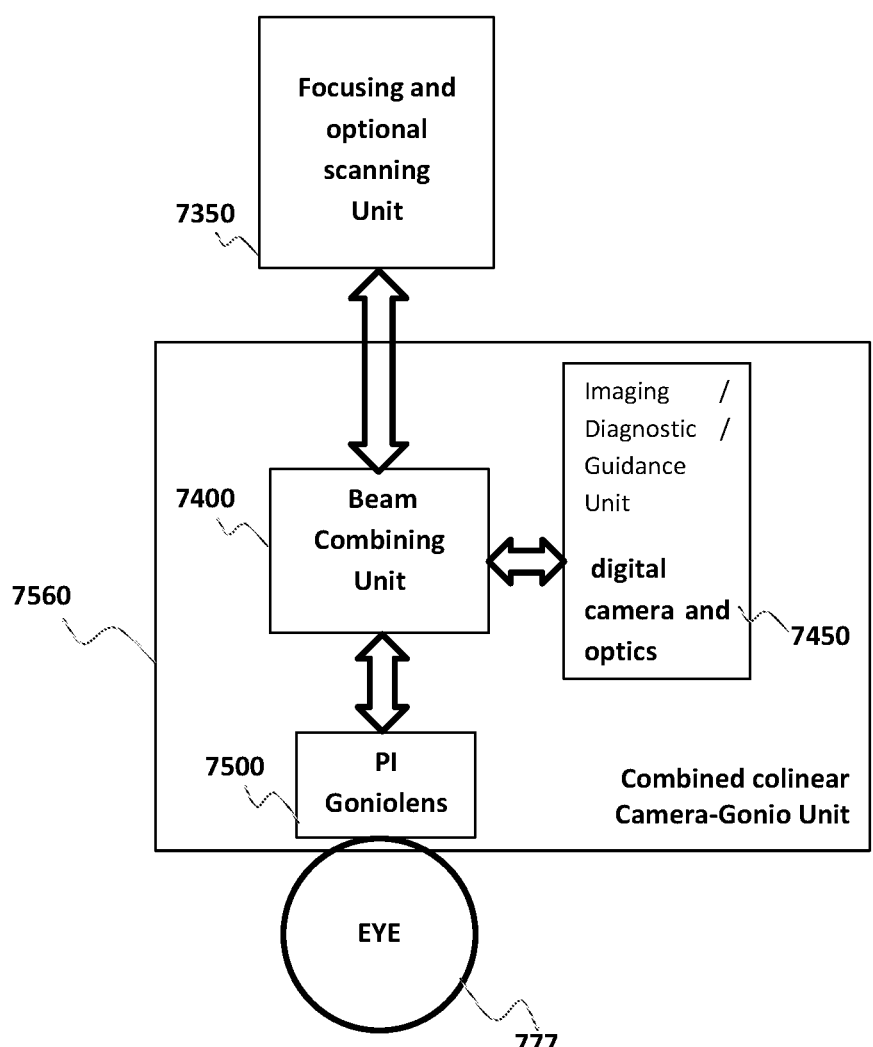
FIG. 5 is a block diagram of a combined colinear camera-gonio unit including a focusing and optional scanning unit, a beam combining unit, an imaging, diagnostic and guidance unit with a digital camera and optics, and a patient interface goniolens, according to some embodiments.
Figure 6:
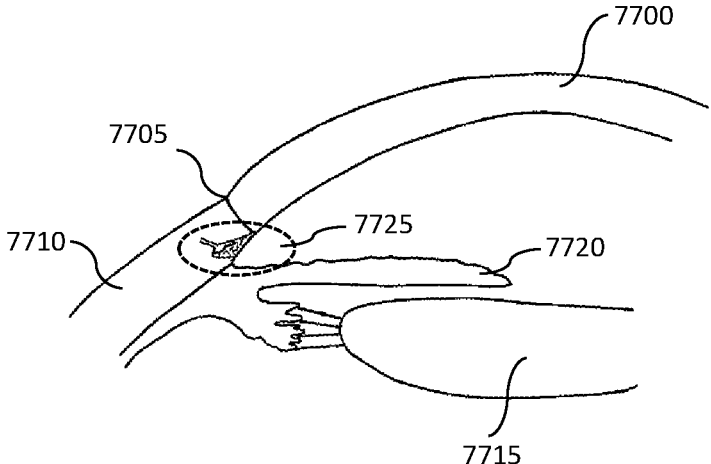
FIG. 6 is a cross-sectional view of an eye showing the cornea, iris, trabecular meshwork, lens, anterior chamber, and sclera, according to some embodiments.
Figure 7:
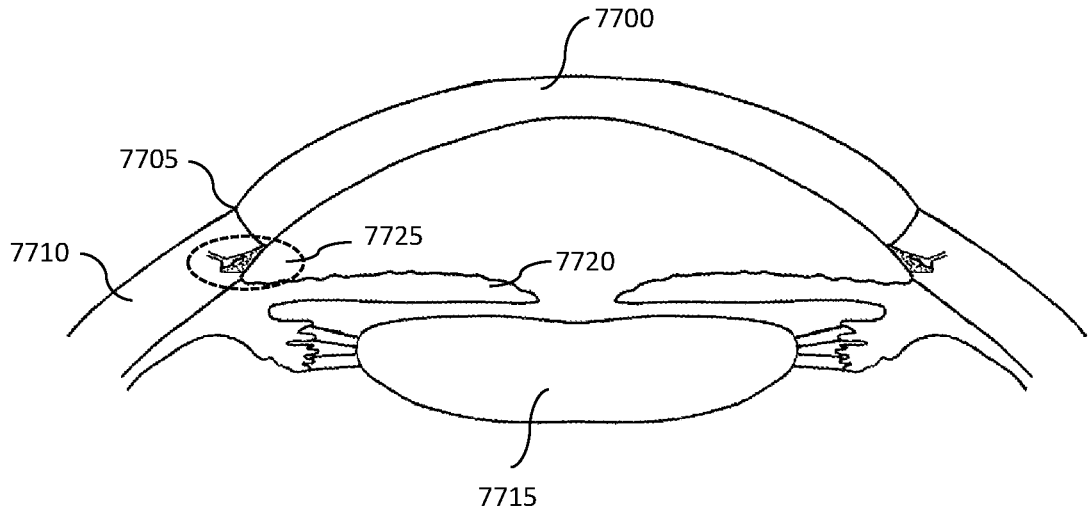
FIG. 7 is a cross-sectional view of an eye showing an anterior chamber angle, according to some embodiments.

A second laser engine with the same parameters as above, that is being controlled independently.

Where the delivery system 7200 consists of the following:

An optional second Imaging/Diagnostic/Guidance Unit FIG. 3, 7250 consisting of one or any combination of the following:

A visual imaging unit 7255 made of one or multiple digital cameras for visible and or non-visible (e.g., infrared) light to capture and process target area visualization data. An integrated visual microscope for direct view of the target area by the operator. A surgical microscope that is integrated with the delivery system. A slit lamp system that is integrated with the delivery system or any combination thereof. These system components are used for visualization and targeting the laser.

An aiming beam light source 7260, such as a single red or other wavelength laser beam that has a strong focusing angle >10 DEG on the target tissue and therefore providing a means to aim for the target tissue laterally (left-right and up-down) as well as an ability to set and calibrate the z-distance which is longitudinal to the laser path and along the axis connecting the proximal extend to the distal extend of the targeted tissue area. This z-calibration is done by placing the focus (smallest spot) of the aiming laser onto or near a defined surface in the eye, for example the proximal surface of the trabecular meshwork here. Another version consists of two or more converging laser beams that meet into one point which is a defined and calibrated point in the z-axis of the laser delivery system. Moving the delivery system components such that the meeting point of these aiming beams falls on the target tissue (e.g. the proximal surface of the trabecular meshwork) will provide z-calibration of the laser system.

An OCT-Imaging system 7265 to use an optical coherence tomography beam for achieving a 3D visualization of the target area.

A two-photon detection system 7265 that is used to analyze fluorescence feedback light that gets emitted by the target area due to two photon interaction of the high peak power treatment laser pulse with the target tissue. This fluorescence feedback diagnostic system is based on the principles of two-photon microscopy. The fluorescence photons that travel back from the target area through the eye, the gonio lens and into a designated detector in the system have a photon energy that is less than two times the treatment laser photon energy. In other words, the wavelength of the fluorescence photons being detected is shorter than the wavelength of treatment laser but longer than ½ of the wavelength of the treatment laser. The feedback signal which is typically very small travels through a narrow optical bandwidth filter designed to transmit the fluorescence wavelength and mostly block other wavelengths. It than lands on a dedicated photodetector. The fluorescence signal photons are created by an interaction of the treatment laser focus and the eye-tissue located at that focus. A small part of these signal photons make it back through the optics system and onto the dedicated photodetector. The signal strength from this photodetector is then recorded and saved together with the momentary target location coordinates of the laser focus. As the laser scans through the target area, the computer and software can then create a 3D imaging map with these individual data points. This fluorescence feedback beam is the used in this invention to create various imaging and calibration data such as laser energy, in particular laser threshold for photodisruptive breakdown, laser pulse duration, laser focusing parameters for example focus size and focus position, optical aberration performance, target tissue surface detections, target tissue depth penetration and target tissue thickness data, target tissue type identification and other tissue interactions with the treatment laser. This imaging scan of the target area by the treatment lase is done with reduced laser power settings and just prior to the actual laser treatment.

A second harmonic beam detection system 7265 with all features as described above in the two-photon microscopy-based detection system, but instead of being based on fluorescence feedback from the two-photon interaction, it is based on a non-linear optical interaction of two photons of the treatment laser beam with the target tissue, creating a frequency doubled photon feedback signal, that has half the wavelength of the treatment laser. Every aspect of the above two-photon fluorescence feedback applies to this method as well. The only difference is a small shift in the feedback wavelength and the signal strength.

A combined two-photon diagnostic system 7265 (two-photon fluorescence and second harmonic) as described in the last two paragraphs above were both the fluorescence feedback photons and the second harmony photons are both detected either together in one detector or in two separate detectors using different optical bandwidth filters. The different signal strength variations from focal point to focal point adds additional image data and resolution to analyze the tissue layers and improved targeting.

A Confocal imaging system 7265 based on the principles of confocal microscopy. This system allows a high-resolution depth penetrating (3D) visualization of the target tissue in the eye.

An imaging system using a digital camera 7265 with one or multiple features as described in the Patient Interface section chapter r. See FIG. 3 as one example (the embodiment of FIG. 16 can be modified to place the camera and illumination behind the big mirror).

An illumination system 7265 with one or multiple features as described in the Patient Interface section chapter r.

A Beam Shaping/Scanning/Combining Unit 7300 consisting of one or any combination of the following:

One or multiple beam shaping optics to modify the laser beam parameters of the treatment laser as it propagates through the delivery system towards the focusing unit. This includes control of the laser beam diameter, convergence angles, astigmatism control and other laser beam parameter. This unit also contains additional optics elements for some or all the above described 7250 imaging, diagnostics and guidance beams that are propagating through the delivery system.

One or multiple scanning optics to create various treatment laser scanning patterns. This includes optical galvo, servo scanners, gimbal mount scanners, micro-scanners, MEMS and other electromechanically driven optical scanners. This unit also contains all the optical scanners that are additionally required for the above described 7250 imaging, diagnostics and guidance beams.

All required optical beam combining elements, for example to combine the laser treatment beam and an alignment laser beam to propagate colinear through the focusing unit and into the eye.

This unit also contains various laser and diagnostic beam sensors to monitor the laser system parameters.

A Focusing and Optional Scanning Unit FIG. 1, 7350 consisting of one or any combination of the following:

A focusing optics assembly to focus the treatment laser beam and all the other imaging, diagnostic and guidance beams towards the target tissue in the eye, consisting of multiple optics elements such as lenses or preferably consisting of a single aspherical lens.

In one embodiment as shown in FIG. 18*b*, the unit 7350 contains a scanning system were the treatment laser beam 7990 is scanned by spinning or translating the focusing optics assembly 7360 or doing both motions together. The focusing optics having a central symmetry axis 7361 parallel but offset to the central optical axis 8030 of the delivery system by the amount of 7362. The spinning part of the scanning having a central spinning axis that is identical with the central optical axis of the delivery system 8030. The focusing optics being oriented such that the incident angle of the central laser treatment beam 7990 is orthogonal (90 deg) to the spinning plane of the focusing lens. All this scanning modes further optionally including a z-axis translation drive/ scan to also scan in the longitudinal z-axis that is colinear with the treatment laser beam.

An optional scannable/tiltable mirror mounted posterior to the focusing optics and therefore closer to the target tissue. That mirror being driven by an electromechanical device and being used as a primary or secondary scanner to perform the desired laser scan pattern in the target tissue. That mirror being preferably mounted in a gimbal mount or being a Micromirror/MEMS based mirror unit or gimbal and MEMS based scanning mirror.

An Optional Second Beam Shaping/Scanning/Combining Unit 7400 consisting of one or any combination of the following:

An additional or primary scanning unit of any type as described in the units 7300 and 7350. This scanning unit having the unique feature of being placed posterior/after the focusing optics unit.

One or more additional optical interfaces and elements including the here above-described scanning unit having the effect of shaping the laser and other beams further in a desired or insignificant way.

A beam combining unit that overlaps and or combines the laser treatment beam with the various optics beams coming in from the Imaging, Diagnostics and Guidance unit 7450 that is placed nearby and delivering all the overlapping and or combined beams into the eye.

An Imaging/Diagnostic/Guidance Unit 7450 consisting of one or any combination of the following:

Any or all the subsystem units from the optional second Imaging, Diagnostic, Guidance Unit 7250

A preferred configuration consists of a slit lamp unit and an optional aiming beam unit where the slit lamp visualization beam path enters directly into the patient interface and is therefore not exactly colinear with the treatment laser beam and the optional aiming beam enters the Beam combining Unit 7400 and becomes colinear with the treatment laser beam.

In another preferred configuration this 7450 unit consists of at least one digital camera with imaging optics and its visualization beam being routed via a beam combining element of the beam combining Unit 7400 between the eye and the camera. Or the camera being mounted in a slightly offset way such that the target tissue imaging beam is captured by the camera in a small angle relative to the treatment laser and therefore does not require a beam combining element and does not travel through unit 7400. The camera and its optics and the entire unit 7450 is connected to the patient interface unit 7500 and if it exists also connected to the Optional second Beam Shaping, Scanning and Combining unit 7400 and therefore Unit 7450+7500 or Unit 7450+7400+7500 become one integrated unit. See, for example, FIG. 26. Unit 7801+8010. Furthermore, this camera having one or multiple features of the camera described at the patient interface unit 7500 chapter r.

Figure 8:
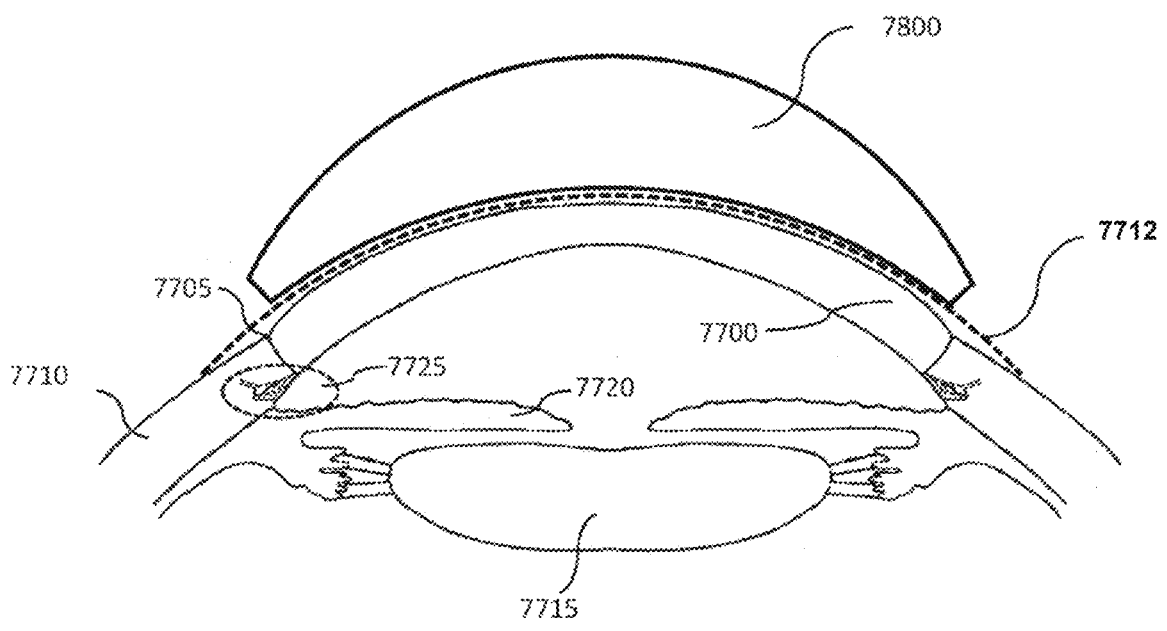
FIG. 8 is a cross-sectional view of an anterior portion of an eye with a goniolens placed on the cornea, according to some embodiments.
Figure 9:
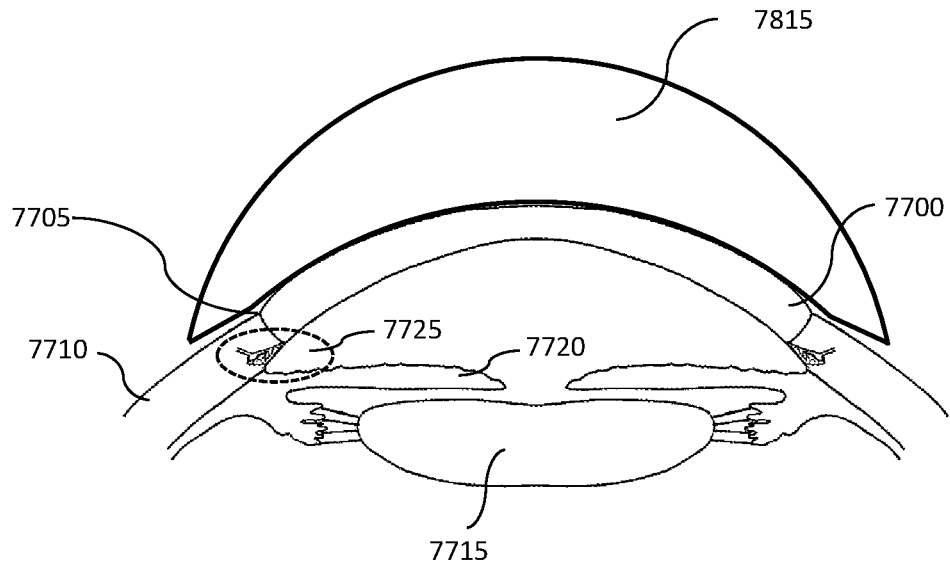
FIG. 9 is a cross-sectional view of an anterior portion of an eye with a goniolens placed on the cornea, according to some embodiments.
Figure 10:
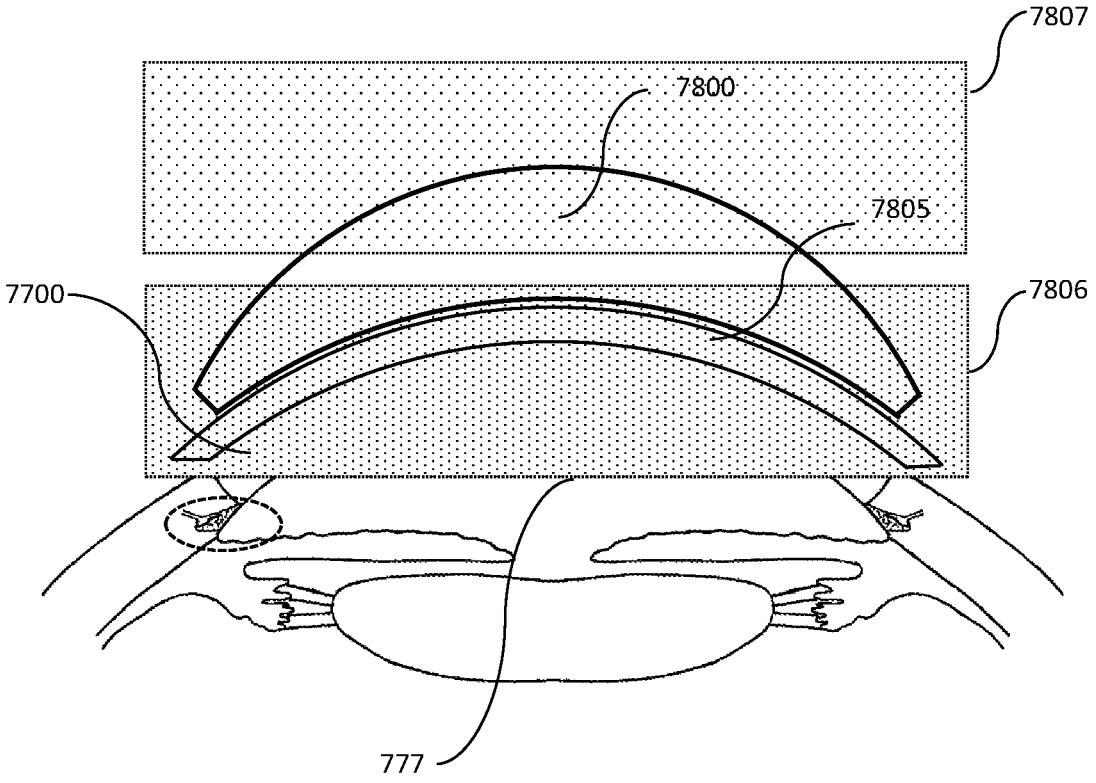
FIG. 10 is a cross-sectional view of an anterior portion of an eye with a goniolens mounted to a glass mounting structure, according to some embodiments.
Figure 11:
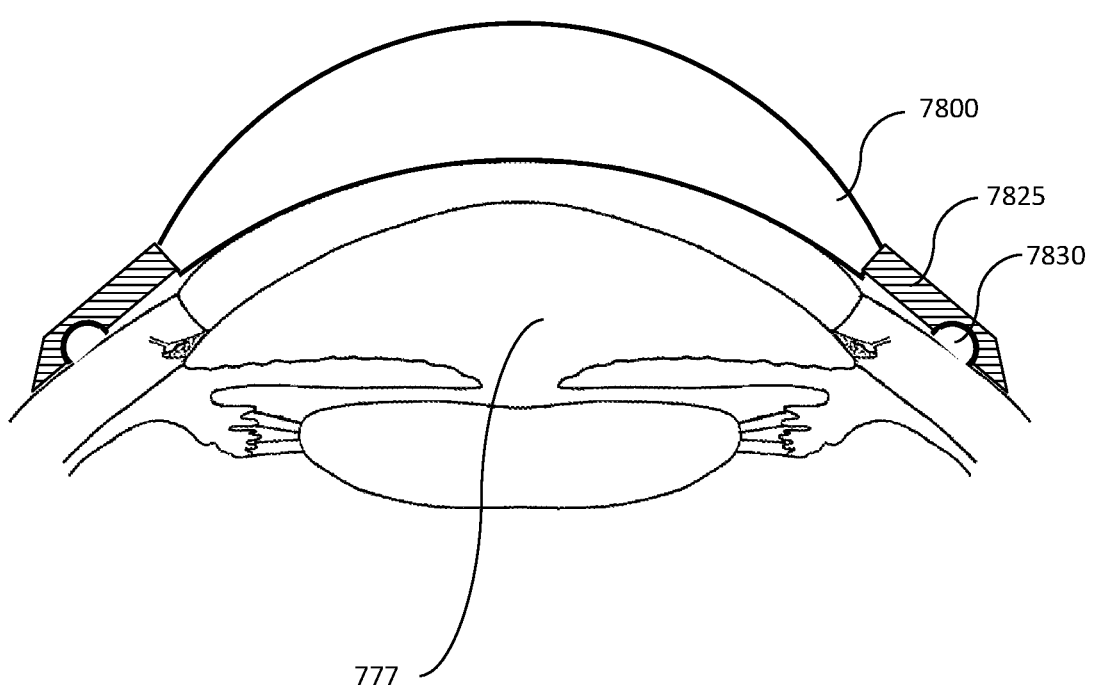
FIG. 11 is a cross-sectional view of an anterior portion of an eye with a goniolens having a flange on an outer rim or an integrated suction ring, according to some embodiments.
Figure 12:
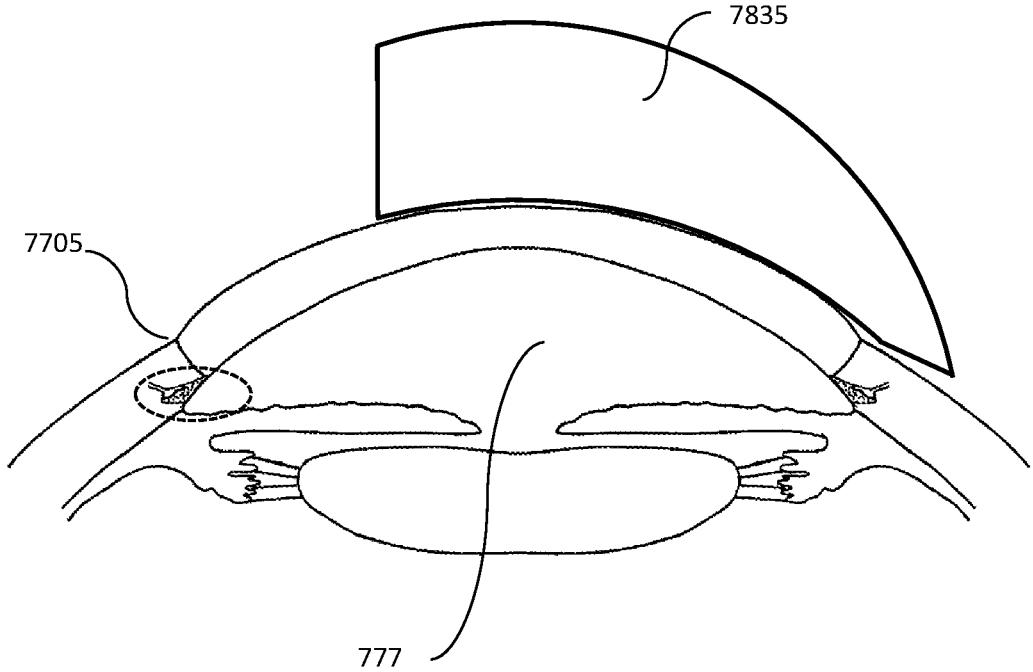
FIG. 12 is a cross-sectional view of an anterior portion of an eye with a goniolens having a cutout above a limbus area where an angle target tissue area is located, according to some embodiments.

A patient interface Unit 7500 consisting of one or any combination of the following:

a. A goniolens with a concave bottom surface to closely fit a human cornea to create an optical interface without minimizing or eliminating any air gap between the goniolens and the cornea. A liquid or gel is optionally applied between the gonio lens and the cornea for better contact.

b. A goniolens as above in a. with a spherical or aspherical convex curvature on the top side to create further focusing and aberration control of the laser treatment beam and diagnostic and visualization beams. Example designs are seen in FIG. 8, 7800 and FIG. 9, 7815.

c. A goniolens as in a. where the at least one side consists of a flat or curved mirror surface and the top surface of the gonio substrate is either flat or curved. See, for example, FIG. 15, 7855 and FIG. 16, 7860. The mirror angle to the horizontal plane is preferably between 60 deg and 70 deg.

d. A goniolens as above b. and optional c. where the substrate has a cutout above the limbus area 7705 where the angle target tissue area 7725 lays. See FIG. 12, 7835. And FIG. 16, 7860. This cutout will not significantly affect the laser beam entering the goniolens and eye since the laser entry into the gonio lens is sufficiently shifted away from this cutout of the gonio lens by being located on the opposite side of the target region such that there is not interference. See FIG. 16 and FIG. 24. In two embodiments FIG. 16 and FIG. 24, this uncovered segment of the cornea and the limbus right over the Treatment area 7725 in the eye that is several millimeters wide is used for additional diagnostic, imaging and treatment beams entering the eye from that side 7880, including entering through the transition zone around the limbus 7705 that consists of the lowest part of the cornea 7770 and the beginning part of the scleral tissue 7710 to probe, visualize and treat the anterior angle tissue region 7725 specifically Schlemm's canal, the trabecular meshwork layers, the Iris, the iris root, the ciliary body tissue, the scleral spur region and the suprachoroidal tissue layers in the eye.

e. A goniolens as in d. where the cutout is large enough to allow access above the target region for an OCT diagnostic and visualization beam 7880, a Two Photon Microscopy beam or another imaging beam that can penetrate the partial scleral tissue layers.

f. Any of the goniolenses above additionally having a flange on the outer rim as shown but not limited to FIG. 11, 7825, that is shaped to fit tight over the transition zone between the cornea and sclera and thereby covers the limbus and continues over the sclera. In another embodiment this flange 7825 has one or more sections cut out to allow access to the limbus in some parts of the eye. This allows for example access to some parts of the eye limbus area where a diagnostic beam is placed as in FIG. 24 as one embodiment.

g. Any of the patient interface configurations above and further adding a sterile clear substrate of a soft material FIG. 8, 7710 or a hard glass material FIG. 10, 7805 with a thickness of <3 mm, being placed between the cornea 7700 and the goniolens 7800 such that it provides a sterile barrier between the eye 777 and the patient interface 7500.

h. A configuration as in g. were that additional optics piece FIG. 8, 7712 is a thin preferably <500 μm thick clear flexible sheet that allows all laser and other beams to travel through without creating significant aberrations. That sheet 7712 being placed on the eye 777 before the goniolens 7800 is place on the eye. Optionally applying a clear liquid or gel below and or above the sheet to make better contact to the eye and the goniolens. That sheet in one configuration being in size such that it only covers the cornea larger that it overlaps over the limbus or beyond covering at least part of the scleral/conjunctival tissue or being large enough to cover the entire eye area of the patient and optionally being connected and integrated with a sterile drape that is being place over at least part of the patient's head.

i. A configuration as in g. were that additional optics piece 7805 is made from glass such as fused silica, Fluoropolymers, BK7 or any other glass that provides a good enough quality to not significantly degrade the laser and other beams transmission. That glass being used in preferably a sterile condition and optionally being single use. That glass being shaped convex on the bottom such that it will make sufficient good contact with the cornea 7700 such that no significant laser and other desired beam degradation occurs. That glass having an upper surface being convex or flat such that it allows docking to the lower side of the goniolens 7800 without any significant or no airgaps in between. Optionally using a clear gel or liquid to improve contact with the cornea and or the gonio lens.

j. A configuration as in i. where the glass is mounted to a structure FIG. 10, 7806 that is being connected and fixed to a gonio mounting structure 7807 above and thereby being placed on the eye 777 together with the entire patient interface or where it is placed on the eye first and then at a later stage in the procedure being docked to the mounting structure 7807 of the gonio lens mount such that it connects in a final aligned fixed position via a docking procedure. Optionally this glass 7805 and its mounting structure 7806 having a built-in flange FIG. 11, 7825 and or an integrated suction ring 7830 that provides further stabilization of the structure.

k. Any of the configurations above and further adding a mounting structure FIG. 24, 8000 around the goniolens 7853 that allows it to be connected to the rest of the laser system delivery system 7200 in a way that it can be attached or detached by the operator. See FIG. 25, 8005 for another embodiment.

l. Any of the configurations above were a suction ring 7830 is integrated with the flange ring 7825 or a stand-alone suction ring to allow a suction stabilized connection between the patent interface 7500 and the eye.

m. Any of the configurations above were the gonio lens unit can be rotated within or together with the patient interface unit in which the goniolens is integrated/mounted in (unless the goniolens by itself is the entire patient interface unit), around the central eye axis 8030 by some degree range greater that 10 degrees and in some configurations by up to 360 degrees before or after being placed on the eye, therefore allowing access to the entire anterior angle of the eye. FIG. 16 to FIG. 26.

n. A configuration as described in above where the gonio lens unit is not docked or connected to the rest of the delivery system and can be rotated independently either by handheld means or by using a separate mounting with its own motorized actuators. FIG. 19, FIG. 20 and FIG. 21.

o. Any of the configuration as described above where the goniolens is a 360 degree fully symmetric optic and this goniolens unit is docked to the rest of the delivery system during the treatment. Furthermore, the beam path being able to rotate 360 degrees by rotating the last routing mirror unit FIG. 25, 8005 containing one routing mirror 7995 or rotating the last routing mirror unit FIG. 26, 8010 containing two routing mirrors 8015 and 8020, before the gonio lens in a circular path around a central eye axis 8030 such that the laser treatment beam rotates 360 degrees and enters the goniolens 7800 and thereby creating a laser entry point into the eye that rotates around the eye symmetry axis. A goniolens unit 7801 consisting of a goniolens 7800 and a mounting unit that is holding the goniolens 7800 and allows for further connections to other units, such as e.g. a suction patient interface 7825 or delivery system components, e.g. mirror units 8005 or 8010. The last routing mirror 8005 or mirrors 8010 unit being rotated while the goniolens unit 7801 and the mirror(s) unit is docked to the rest of the delivery system including a rotational joint. Furthermore, this configuration including an optional second rotational joint between the gonio lens unit 7801 and the mirror(s) unit 8005 or 8010 to allow the mirror(s) unit being rotated around the goniolens unit 7801, while said goniolens unit is being fixed to the eye via suction and while all units are mechanically docked or permanently connected to the rest of the delivery system.

p. A configuration as in FIG. 25 were a combining/mirror unit 8005 including an optional camera and illumination unit 7853 as described in chapter r. below, is permanently connected to a goniolens unit 7801 and were the combined unit 8005+7801 is detached from the rest of the delivery system 7989 prior to the treatment procedure and were said combined unit is placed and moved on the eye, preferably by hand establishing a connection between the goniolens 7800 and the eye 777 and aligning through translation and rotation of the combined unit the central imaging beam path 7779 to the desired target area in the anterior angle of the eye using the optional camera unit 7853 or other visual means. Following this alignment, the combined unit 8005+7801 being optionally fixed to the eye using a suction device similar or identical to the configuration in FIG. 11 or continues to be handheld in place while the rest of the delivery system 7989 now being placed over this combined unit and aligned such that the central laser treatment beam 7990 becomes colinear or close to colinear with the central imaging beam path 7779. The rest of the delivery system 7989 now being docked and connected to the combined unit 8005+7801 or remaining unconnected in this pre-aligned position. The laser system now finalizing the targeting alignment using imaging and diagnostic data to auto align the laser target or performing alignments via operator input. After completing alignment, the laser treatment being initiated and completed.

q. A configuration as in FIG. 26 were a mirror unit 8015 including an optional camera and illumination unit 7853 as described in chapter r. below, is permanently connected to a goniolens unit 7801 and were the combined unit 8015+7801 is detached from the rest of the delivery system 7989 prior to the treatment procedure and were said combined unit is placed and moved on the eye, preferably by hand establishing a connection between the goniolens 7800 and the eye 777 and aligning through translation and rotation of the combined unit the central imaging beam path 7779 to the desired target area in the anterior angle of the eye using the optional camera unit 7853 or other visual means. Following this alignment, the combined unit 8005+7801 being optionally fixed to the eye using a suction device similar or identical to the configuration in FIG. 11 or continues to be handheld in place while the rest of the delivery system 7989 now being placed over this combined unit and aligned such that the central laser treatment beam 7990 becomes colinear or close to colinear with the central imaging beam path 7779. The rest of the delivery system 7989 now being docked and connected to the combined unit 8005+7801 or remaining unconnected in this pre-aligned position. The laser system now finalizing the targeting alignment using imaging and diagnostic data to auto align the laser target or performing alignments via operator input. After completing alignment, the laser treatment being initiated and completed.

r. Any of the patient interface configurations above and further adding a digital camera and its imaging optics and integrating it in the patient interface unit in the following configurations:

1. FIGS. 17, 24, 25, and 26 shows a goniolens 7855, 7853 or 7800 laying on an eye, the treatment and diagnostic beams 7990 are coupled into the gonio lens and eye via a mirror. Said mirror being at least partially transmissible to the wavelength range that the digital camera is sensitive to, a digital camera with imaging optics being mounted behind that mirror such that the target region of the laser system is imaged through the gonio lens, the mirror, the camera imaging optics 7895 and onto the digital camera sensor 7905. The camera unit 7853 housing being connected or integrated to a gonio unit mounting. See for example FIG. 17, 7880. The connected or integrated camera unit being either fixed or being adjustable in 3 dimensions to allow for mechanical alignments such that a calibrated vision of the target area relative to the treatment and other beams being reflected by the mirror is achieved. Therefore, allowing lateral x, y alignment and calibration as well as focus, defined as z here, adjustments.

2. A configuration as in r.1. above where the patient interface unit is fixed connected to the rest of the delivery system mounting. For example, FIG. 24, the patient interface unit 8000 being fixed connected to the rest of the delivery system 7989.

3. A configuration as in r.1. above where the patient interface unit is initially decoupled from the rest of the delivery system mounting, and then after it has been placed on the eye with or without suction, being docked to the rest of the delivery system and then creating a fixed combined unit. For example, FIG. 26, the patient interface sub units 7801 and 8010 initially being decoupled from each other and from the rest of the delivery system 7989 and then after alignments all being docked and connected to each other 7801+8010+7989.

4. FIG. 24, 25, or 26 showing a gonio lens 7853 or 7800 laying on an eye, the treatment and diagnostic beams are coupled into the gonio lens and eye via a final mirror 7995 or 8020. Said mirror being at least partially transmissible to the wavelength range that the digital camera is sensitive to, a digital camera with imaging optics 7853 being mounted behind that mirror such that the target region of the laser system is imaged through the gonio lens, the mirror, the camera imaging optics 7895 and onto the digital camera sensor 7905. The camera unit 7853 housing being connected or integrated to the mirror unit 8000, 8005 or 8010 but not to the gonio unit 7801. Therefore, the gonio lens unit being mounted separate from the rest of the patient interface unit including the option to not being mounted at all and rather handheld via some mechanical feature such as a handle or fixed to the eye by a suction device. At the same time, the integrated camera, mirror unit 8000, 8005 or 8010 being mounted to the rest of the delivery system 7989. The camera and imaging optics unit 7853 being integrated with the mirror unit either fixed or being adjustable in 3 dimensions, x, y and including focus z relative to the mirror unit to allow for its vision axis propagating through the mirror to be adjusted to become collinear to the treatment laser beam 7990 after being reflected by the mirror and propagating towards the eye and its focus z being calibrated to the treatment laser focus at some offset including zero. In this configuration the patient interface unit up to and including the camera and mirror unit is separately adjustable via system motion motors or by hand and the gonio unit, being separately adjustable by hand or through system motion motor that are movable independently from the rest of the patient interface. After target alignment, a laser treatment being performed while the goniolens unit 7801 remains unconnected to the mirror unit 8000, 8005 or 8010.

5. A configuration as in j. were the glass mounting structure is integrated with a digital camera and its imaging optics such that the camera and optics unit is fixed or adjustable relative to the mounting structure and that is aligned to image the target area once the glass has been connected or docked to the gonio lens unit.

6. A configuration as in j. were the glass mounting structure is integrated with a digital camera and its imaging optics such that the camera and optics unit is fixed or adjustable relative to the mounting structure and that is aligned to image the target area once the glass has been connected or docked to the gonio lens unit.

7. Any of the gonio lens configurations above where a camera is integrated inside or near the gonio lens in a way where the central visualization axis is slightly offset from the treatment laser. Furthermore, the camera and its imaging optics being very small, preferably having a physical size in the two dimension perpendicular to the imaging beam direction of <10 mm. Therefore, the camera location being placed in a direct optical path between the camera and the target area in the eye without having to propagate through a beam combiner mirror. The treatment laser beam and other beams propagating next to the optical path of the camera preferably through the main symmetrical axis of the goniolens and onto the target area of the eye to minimize aberrations for the treatment laser.

8. FIG. 17. A one-piece mirrored goniolens 7855 were a small camera and its imaging optics 7853 including optional digital camera and or illumination sources 7885 are integrated inside the goniolens unit 7880 or right behind the mirror to either allow direct imaging or an imaging path through the at least partially transmissible goniolens mirror 7891 and imaging towards the back of the eye using the camera/illumination unit 7885. If said mirror is placed at an angle were total internal reflection occurs for the imaging beam, therefore not allowing any beam part to transmit to the camera, then an optional coated prism 7890 is installed right behind the mirror such that it makes an optical contact with the back side of the mirror and therefore allows some part of the imaging beam being transmitted through the mirror 7891, through the prism 7890 and into the camera unit 7853.

9. Any of the camera configurations above and furthermore the camera having a high sensitivity, therefore allowing to minimize the illumination level into the target area and still providing clear pictures and videos.

10. Any of the camera configurations above and furthermore the camera operating at an infrared wavelength or any other range that is not visible to the human eye. In particular, a wavelength range that does not trigger significant constriction of the pupil while the target area is illuminated by lighting in such a wavelength range.

11. Any of the camera configurations above and their output being directed to illuminate the target area in the eye and such illumination being preferably adjustable in power and optionally in wavelength (one or multiple) to modify the contrast of certain tissue layers in the target area that have different absorption and emission properties for different wavelengths of light. By changing the wavelength of the illumination source different features of the target tissue area are being highlighted or suppressed, such as the pigmented and non-pigmented trabecular meshwork, Schwabe's line, the scleral spur, the iris, an open backwall section of the Schlemm's canal and other anatomical features. This will help the operator watching the camera output on a screen or an automated vision system connected or integrated with the laser system to get more information about the target tissue area of the patient's eye.

12. One or multiple light sources as described above where the preferred light source is either a led source or a fiber coupled led light source or a laser light source or a fiber coupled laser light source.

13. An additional optional adjustable light source that is mounted anywhere in the delivery system and aligned such that it provides a light beam entering the gonio lens in the central region such that the illumination propagated through the iris of the eye and terminating on the retina of the eye. This light source is used to stimulate an iris contraction response in the patient's eye were based on the adjusted power level of this light source and spot size on the retina, a stronger or weaker iris pupil closing effect can be achieved. As the iris pupil closes more, the iris root close to the anterior angle structures gets pulled away from the angle and thereby opens up the angle more. This allows for easier and more access of the target tissue area in the anterior angle of the eye for the treatment laser, any diagnostic beam, any imaging and visualization beam and any illumination for the angle tissue. FIGS. 17, 20, 21, 22, 23, 24, 25, and 26 show such an embedded light source 7885 which optionally also includes a camera to image the iris, the lens/capsule and retina of the eye, integrated in the patient interface along the central axis of the eye.

14. Any of the camera configurations above where the camera and its imaging optics have a small physical size comparable or smaller than a camera and optics combination of a typical smart phone. The preferred size of the camera and optics combination being <10 mm in each axis.

15. Any of the camera configurations above where the camera and its imaging optics has a larger size such that its housing can be used as a handle to move the integrated camera gonio unit. A preferred length of the camera housing 7920 length is >15 mm. See FIG. 19 and FIG. 21, 7920 for some embodiments.

16. Any of the camera configurations above where the imaging optics further has a zoom capability to change the magnification of the image.

17. Any of the camera configurations above where a camera output signal is connected to a laser system computer via a cable or via a wireless connection and where the imaging data of this output signal is used to verify and control system parameters before, during and after the treatment. See FIG. 22, 7946, 7948 for one embodiment. Optionally unit 7948 further including a battery for power, electronic drivers and an embedded computer and software to control the cameras, illuminations and to preprocess and store the imaging data.

s. Any of the configuration as in FIGS. 24, 25, and 26 where an additional focusing unit is located between the gonio lens and the laser routing mirror(s).

t. Any of the configuration as in FIGS. 24, 25, and 26 where any or all of the laser routing mirrors is a curved mirror, such that it adds to the focusing and aberration control of the delivery system.

u. Any of the configuration as in FIGS. 24, 25, and 26 where any or all of the laser routing mirrors is a mechanically tiltable mirror, such that it adds to or replaces the scanning systems of the delivery system.

A standalone Goniolens with an integrated digital camera and imaging optics referred to from here on as the camera-gonio unit.

In one embodiment the camera-gonio unit consisting of a direct gonio lens without any mirror and having its camera either integrated within the optical gonio substrate FIG. 22 (camera units 7960 and 7955 and illumination units 7965 and in 7955) or being mounted next to the gonio substrate FIG. 19, 7915, FIG. 20, 7925, FIG. 21, 7930 or FIG. 24, 8000 and the camera having an alignment that provides an image of the anterior angle of the eye when the unit is placed on the eye. A second optional camera is placed at location that allows a straight down view to the retina area of the eye for retinal imaging of the eye. FIG. 22, 7955.

FIGS. 22 and 23. In one embodiment the camera-gonio unit 7950 consisting of a direct gonio lens without any mirror and having its camera integrated within the optical gonio substrate. FIG. 22 showing the integrated camera units 7960 for anterior angle visualization, camera unit 7955 for iris, lens in the eye and retina visualization, and illumination units 7965 and inside or next to 7955. An optional handle or grabbing features on the unit 7950 allows this unit to be moved on the eye. It is being rotated to image all parts of the 360 deg angle tissue in the eye, as well as being moved up and down and sideways on the cornea to adjust the lateral view position of the central camera 7955, as well as the visualization approach of camera 7960 into the irido-corneal angle region of the eye. FIG. 23 showing an exploded view of FIG. 22 were all camera and illumination units float above their integrated positions over the specifically shaped goniolens 7970 that contains a standard concave bottom surface and an irregular shaped upper surface that is shaped such that it provides aligned window surfaces that accept the individual modules so that their aiming direction into the eye is preset and prealigned. The goniolens 7970 shape is specifically manufactured to accommodate a specific set of camera and illumination units that are selected to be integrated in this unit.

In another embodiment the camera-gonio consisting of a mirrored gonio lens and having its camera either integrated within the optical gonio substrate or being mounted next to the gonio substrate and in this case the optical path of the camera entering the gonio lens mirror from above.

Any of the above camera-gonio unit having an additional holding stick or grip features integrated in a housing such that the unit can be held and manipulated by hand.

Any of the above camera-gonio unit having an additional mounting flange with an integrated suction ring to allow the camera-gonio unit to be held in place on the eye without the operator having to hold it with a hand.

Any of the above camera-gonio unit with the camera and imaging unit being a small unit <10 mm in all 3 dimensions or at least 2 of 3 dimensions.

Any of the above camera-gonio unit with the camera and imaging unit being a larger unit >10 mm in length and optionally including a zoom lens. The body of the camara housing being optionally used as a handle to manipulate, move and adjust the camera-gonio unit on the eye. See for example FIG. 19 and FIG. 21 or FIG. 25 were a large camera 7920 is integrated above the mirror 7995.

Any of the standalone camera-gonio units above where the camera signal is transmitted to a display or a computer system of any other imaging, diagnostics, or treatment system through a electrical cable.

Any of the standalone camera-gonio units above were the camera pictures and videos are recorded on a memory device that is integrated in the standalone camera-gonio unit.

Any of the standalone camera-gonio units above where the camera signal is transmitted to a display or a computer system of any other imaging, diagnostics, or treatment system through a wireless transmission and optionally is powered by an integrated battery.

Any of the standalone camera-gonio units above additionally containing one or multiple of the following illumination sources:

One or multiple light sources with visible or infrared wavelength 830 output is mounted separate or within the camera housing and its output being directed to illuminate the target area in the eye and its power being preferably adjustable in power and optionally, in wavelength to modify the contrast of certain tissue layers in the target area that have different absorption and emission properties for different wavelengths of light. By changing the wavelength of the illumination source different features of the target tissue area can be highlighted or suppressed, such as the pigmented and non-pigmented trabecular meshwork, Schwabe's line, the scleral spur, the iris, an open backwall section of the Schlemm's canal and other anatomical features. This will help the operator watching the camera output on a screen or an automated vision system connected or integrated with another system to get more information about the angle tissue area of an eye.

One or multiple light sources as described above where the preferred light source is either a led source or a fiber coupled led light source or a laser light source or a fiber coupled laser light source.

An additional optional adjustable light source that is mounted and aligned that it provides a light beam entering the gonio lens in the central region, e.g., FIG. 22, 7955 such that the illumination propagated through the iris of the eye and terminating on the retina of the eye. This light source is used to stimulate a iris contraction response in the patients eye were based on the adjusted power level of this light source and spot size on the retina the a stronger or weaker iris pupil closing effect can be achieved. As the iris pupil closes more, the iris base close to the anterior angle gets pulled away from the angle and thereby opens up the angle more. This allows for easier and more visibility in the anterior angle of the eye. FIG. 22 shows such a light source integrated in the gonio camera unit.

Any of the above camera-gonio units where the unit is part of a patient 860 interface that is either permanently connected to a laser delivery system or detachable and dockable to a laser delivery system. FIGS. 17, 24, 25, and 26 show the here embodied versions that provide a dockable or permanent mechanical connection to a laser delivery system 7989. The unit in FIG. 26 has the additional feature that the laser input beam enters centered and parallel to the main symmetry axis of the eye and therefore allows access to all 360 degrees of irido-corneal angle tissue of the eye by rotating the two-mirror assembly 8010 around this center axis. In one version the mechanical connection of the entire connected unit 8010+7801 connects to the rest of the laser delivery system above 7989 via rotatable joint. In another version there is an additional rotatable interface joint between the two-mirror unit 8010 and the goniolens unit 7801, therefore allowing the goniolens to remain stationary on the eye and fixed via a suction device, while the rest of the patient interface above rotates to allow full 360 deg access to the anterior angle of the eye. Other than the rotational joints all units 7801+8010+7989 are here fixed connected and no docking procedure is being performed. The entire combined unit 7801+8010+7989 is preferably being moved and placed on the eye by hand and then is held in place during the treatment procedure either by hand or via a suction device.

A patient interface unit where one side of the goniolens is cut off as in FIGS. 16, 19, 20, 21, 22, and 24 thereby opening up access to the limbus area and part of the cornea over the target zone that is defined by the laser or imaging beams entering the goniolens from the other side. These cutout versions being used in a system that contains diagnostic, imaging and or treatment beams that enters the limbus area over the target area from above as described below. See FIG. 16 or FIG. 24.

FIG. 24. A system where the target area at the anterior angle area of the patient's eye is treated via a treatment laser beam 7990 coming through a gonio lens 7853 and therefore entering the cornea of the eye on the opposite side from the target area 7725. At the same time providing pre-op, during treatment and post-op diagnostics and imaging of the target area 7725 by penetrating the tissue layers in the area right above the target area with a one or multiple diagnostic and imaging beams 7880. The tissue layers above the target area are around the limbus 7705 and consist of sclera tissue 7710, conjunctival tissue and outer cornea tissue layers in 7770. See FIG. 28. The tissue layers other than the cornea tissue cannot be easily penetrated by light sources including lasers. Particularly the scleral tissue layers 7710 can cause a large amount of light scattering, absorption and aberrations. The amount of beam degradation because of scattering, absorption and aberrations is wavelength dependent. The here presented systems 7882 such as in FIG. 24 are used to penetrate this tissue area of the eye and provide useful diagnostics and imaging data. It is well known that Optical Coherence Tomography can penetrate scattering and absorbing tissue layers. In one configuration, an OCT beam 7880 is used to penetrate the tissue layers entering the eye anywhere between 5 mm up from the limbus into the cornea and 10 mm down from the limbus into the sclera from here on referred to as the entry area. The OCT beam enters the eye at an angle that is parallel to the main optical axis of the eye or tilted from this vertical axis by up to 60 degrees to either side. This OCT imaging beam provides data that allows for imaging and visualization of the tissue layers in the target region of the eye, including the outline, size and location of the layers of Meshwork 7907, Schlemm's canal 7945 and other tissue layers. This data is then used by the operator to assess the target area 7725 and prepare the treatment parameters. In one embodiment this data is used to assess the shape and integrity of Schlemm's canal 7945. As demonstrated in FIG. 28 showing a healthy eye or an eye in an early glaucoma stage the Schlemm's canal width in the radial axis of the eye is much larger than in an eye that has more tissue degradation due to more advance glaucoma and has a partially collapsed Schlemm's canal 7945 in FIG. 27. This information is optionally used to adjust the laser treatment parameter. Furthermore, the OCT data is used to calibrate and guide the laser treatment in the target area either by a fully automated image analyzation system that adjusts and sets the system parameters before and during the treatment procedure, or by providing the data displayed on a monitor, such that the operator can make system parameter adjustments based on the measured OCT data or a combination of both.

Furthermore, the OCT or two-photon imaging data is used after the laser procedure to visualize, measure and analyze the laser treatment effects on the target tissue layers.

Based on the OCT beam location through the limbus area the quality of the OCT imaging data will vary. For example, by aligning the OCT beam to enter in the region of the transition zone between the cornea and the sclera, see FIG. 28, 7880 the OCT beam 7880 has an easier and higher penetration ability since less of the scattering tissue 7711 (sclera starting part) is in its beam path. This allows for an easy detection of particularly the upper regions of the trabecular meshwork 7905. And that data is then used to calibrate the system parameters including monitoring this data live during the laser treatment and making laser system adjustment during the treatment to accommodate or compensate any movement or changes of the treated tissue layers.

In one embodiment the OCT beam 7880 is propagating into the eye via the entry area, described above without any optical interface connected to the eye, therefore enter the eye tissue layers from the air. FIG. 24.

In another embodiment a glass or clear material substrate 7883 is placed over at least part of the entry area such that the OCT beam 7880 is propagating into the entry area of the eye via said substrate. See FIG. 24.

In another embodiment this OCT imaging system is integrated into the laser treatment system in a way that it shares at least a control system part or a user interface part or a delivery system part or any combination thereof.

In another embodiment, this OCT imaging system unit 7882 is mechanically connected to a patient interface, e.g., FIG. 24, 8000 that is configured to allow the OCT beam to enter the eye through the entry area while simultaneously allowing the treatment laser beam 7990 to enter the eye 777 through the gonio lens 7853 around the opposite side of the cornea. See FIG. 24.

FIG. 24A dual patient interface consisting of at least a gonio lens being mechanically mounted to a housing part 8000 of the patient interface that makes contact with the eye and allows a treatment beam 7990 to enter the eye from one side and having a cutout, open access area at the limbus area referred to earlier as the entry area on the side opposite to the treatment laser entry of the eye. This housing cutout opening in the patient interface, being positioned above the treatment target area of the eye allowing an OCT imaging beam entering the eye through an optional substrate 7883 that lays on the limbus area and that substrate 7883 being optionally integrated and mechanically connected to the housing 8000.

This dual patient interface where the mechanical housing 8000 is further connected to at least part of the OCT imaging beam delivery system optics, part of 7882.

In another embodiment the OCT imaging beam as described above is part of a standalone diagnostic system that is used independent from any treatment system and optionally also independent from any gonio lens imaging unit.

In another embodiment this standalone system containing a scanning system that scans the OCT beam in addition to the target tissue area also around at least part or all of the circumference of the entire circular limbus area of a patient's eye to create imaging data of part or all of the eye's anterior angle area.

An OCT imaging system configuration as described above were instead of OCT a two-photon microscopy detection system or a second harmony detection system or any combination of these detection systems is used.

The invention claimed is:

1. A modular goniolens assembly for visualizing and treating an anterior angle region of an eye, the assembly comprising:
    a housing component configured to permit the assembly to be handled by a physician, the housing component having one or more individual modules for illuminating and/or visualizing the eye and a battery for powering the one or more individual modules; and
    a goniolens body coupled to the housing and having a contact surface adapted to contact a cornea of the eye and an irregular shaped upper surface, opposite the contact surface, that provides aligned window surfaces that accept one or more individual modules in a predetermined alignment such that an aiming direction into the eye of the one or more individual modules is preset
    to enhance visibility of the anterior angle region;
    wherein the housing component is removably couplable to the goniolens body for aligning the one or more individual modules relative to the goniolens body; and
    wherein the goniolens assembly is configured to provide standalone illumination and/or visualization of the anterior angle region and to facilitate delivery of laser treatment pulses to the anterior angle region.

2. The assembly of claim 1, further comprising a mechanical docking interface configured to detachably connect the goniolens assembly to a main laser console.

3. The assembly of claim 2, wherein the mechanical docking interface comprises an alignment feature ensuring co-linearity of a treatment laser beam with an optical axis of the goniolens body.

4. The assembly of claim 1, wherein the one or more individual modules comprises a digital camera integrated with the goniolens body and oriented to capture images of the trabecular meshwork.

5. The assembly of claim 4, wherein the digital camera is configured to wirelessly transmit real-time video to an external display or control system when the assembly is undocked.

6. The assembly of claim 4, wherein the goniolens body comprises an internal reflective surface configured to redirect a portion of the laser beam toward the trabecular meshwork while transmitting light to the digital camera.

7. The assembly of claim 1, further comprising a handle extending from the goniolens body to facilitate handheld manipulation and rotation around the eye's optical axis.

8. The assembly of claim 1, wherein the one or more individual modules comprises an illumination source that includes at least one LED array emitting both visible and infrared wavelengths for selective tissue contrast enhancement.

9. The assembly of claim 1, wherein the mechanical docking interface includes a locking mechanism that engages automatically upon axial alignment with the main laser console.

10. The assembly of claim 1, further comprising a sterile barrier element attached to the contact surface, the sterile barrier element being disposable after a single use.

11. The assembly of claim 1, wherein the one or more individual modules comprises an illumination source that is arranged to project light onto a retina of the eye to induce partial pupil constriction and thereby expose more of the trabecular meshwork to the digital camera.

12. An integrated ophthalmic system for diagnostic imaging and laser treatment of an anterior angle region of an eye, the system comprising:

a laser module generating ultrashort pulses for selectively disrupting trabecular meshwork tissue;

a goniolens having a contact surface for coupling with the cornea and an integrated mirror to direct the laser beam to the anterior angle region, the goniolens having an irregular shaped upper surface, opposite the contact surface, against which an illumination module and a camera module are supported in a plurality of alignment positions;

an imaging unit configured to direct at least one of an OCT beam or a confocal beam into the eye;

an operator user interface comprising a switch for activating the laser module and a display for showing images captured by the camera module; and a system controller configured to coordinate the laser module, the camera module, and the imaging unit to enable combined diagnostic imaging and targeted laser application to the trabecular meshwork.

13. The system of claim 12, wherein the system controller automatically merges real-time images from the camera module with depth information from the imaging unit for enhanced surgical guidance.

14. The system of claim 12, wherein the integrated mirror in the goniolens is coated to reflect the wavelength of the laser module while transmitting light within a visible or near-infrared band to the camera module.

15. The system of claim 12, further comprising a foot switch operatively coupled to the operator user interface provides variable vibrational feedback indicating different laser pulse energy levels.

16. The system of claim 12, further comprising a flange configured to accommodate a suction ring for stabilizing the goniolens against the cornea during laser application.

17. The system of claim 12, further comprising a rotating mirror assembly disposed between the laser module and the goniolens, the rotating mirror assembly being adapted to pivot the laser beam around at least 180 degrees of the trabecular meshwork circumference.

18. The system of claim 12, wherein the imaging unit comprises a confocal fluorescence detection device arranged to detect fluorescent emissions from trabecular meshwork tissue when excited by low-power scanning.

19. The system of claim 12, wherein the laser module is configured to generate pulses in a femtosecond to nanosecond range and deliver them at a repetition rate of up to 500 KHz.

20. The system of claim 12, further comprising a memory module configured to record both real-time video from the digital camera module and the imaging data from the imaging unit for post-operative analysis.

\* \* \* \* \*